US 7,736,873 B2

(12) United States Patent
Murdin et al.

(10) Patent No.: US 7,736,873 B2
(45) Date of Patent: Jun. 15, 2010

(54) ***CHLAMYDIA* POLYPEPTIDES AND CORRESPONDING DNA FRAGMENTS AND USES THEREOF**

(75) Inventors: Andrew D. Murdin, Richmond Hill (CA); Raymond P. Oomen, Aurora (CA); Joe Wang, Toronto (CA); Pamela Dunn, Woodbridge (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 217 days.

(21) Appl. No.: 11/932,276

(22) Filed: Oct. 31, 2007

(65) Prior Publication Data

US 2009/0142376 A1 Jun. 4, 2009

Related U.S. Application Data

(60) Division of application No. 10/324,129, filed on Dec. 20, 2002, now Pat. No. 7,326,545, which is a continuation of application No. 09/452,380, filed on Dec. 1, 1999, now abandoned.

(60) Provisional application No. 60/110,439, filed on Dec. 1, 1998, provisional application No. 60/132,272, filed on May 3, 1999.

(51) Int. Cl.
| C12P 21/04 | (2006.01) |
| A61K 39/118 | (2006.01) |
| C07K 14/195 | (2006.01) |
| C07K 14/295 | (2006.01) |
| C12P 21/06 | (2006.01) |

(52) U.S. Cl. .................. 435/69.7; 435/69.1; 424/263.1; 536/23.1; 536/23.7; 530/300; 530/350

(58) Field of Classification Search ........................ None
See application file for complete search history.

(56) References Cited

U.S. PATENT DOCUMENTS

| 5,525,463 | A | 6/1996 | Zolg |
| 5,629,167 | A | 5/1997 | Ratti |
| 6,521,745 | B1 | 2/2003 | Murdin et al. |
| 6,559,294 | B1 | 5/2003 | Griffais et al. |
| 6,693,087 | B1 | 2/2004 | Murdin et al. |
| 6,808,713 | B1 | 10/2004 | Murdin et al. |
| 6,822,071 | B1 | 11/2004 | Stephens et al. |
| 7,019,125 | B2 | 3/2006 | Murdin et al. |
| 7,070,792 | B2 | 7/2006 | Murdin et al. |
| 7,081,245 | B2 | 7/2006 | Murdin et al. |
| 2002/0082402 | A1 | 6/2002 | Murdin et al. |
| 2002/0094965 | A1 | 7/2002 | Murdin et al. |
| 2002/0099188 | A1 | 7/2002 | Murdin et al. |
| 2002/0132994 | A1 | 9/2002 | Murdin et al. |
| 2003/0100706 | A1 | 5/2003 | Murdin et al. |
| 2004/0254130 | A1 | 12/2004 | Murdin et al. |

FOREIGN PATENT DOCUMENTS

| EP | 319944 | 7/1988 |
| EP | 592894 | 1/1993 |
| EP | 430930 | 12/1996 |
| EP | 0784059 | 7/1997 |
| WO | WO 98/02546 | 1/1998 |
| WO | WO 98/58953 | 12/1998 |
| WO | WO 99/27105 | 6/1999 |
| WO | WO 99/28475 | 6/1999 |
| WO | WO 00/24765 | 5/2000 |
| WO | WO00/27994 | 5/2000 |
| WO | WO 00/34483 | 6/2000 |
| WO | WO 00/37494 | 6/2000 |
| WO | WO 00/46359 | 8/2000 |
| WO | WO 00/66739 | 11/2000 |
| WO | WO 01/21804 | 3/2001 |
| WO | WO 01/21811 | 3/2001 |
| WO | WO 01/40474 | 6/2001 |
| WO | WO 01/46224 | 6/2001 |
| WO | WO 01/81379 | 11/2001 |
| WO | WO 01/85972 | 11/2001 |
| WO | WO 02/02606 | 1/2002 |
| WO | WO 02/08267 | 1/2002 |

OTHER PUBLICATIONS

Lederman et al (Molecular Immunology 28:1171-1181, 1991).*
Li et al (Proc. Natl. Acad. Sci. USA 77:3211-3214, 1980).*
Houghten et al. (Vaccines, 1986, Edited by Fred Brown: Cold Spring Harbor Laboratory).*
Holmes, Exp. Opin.Invest. Drugs, 2001, 10(3):511-519).*
Greenspan et al (Nature Biotechnology, 1999, 7:936-937).*
U.S. Appl. No. 09/857,128, filed Sep. 20, 2001, Murdin et al.
U.S. Appl. No. 09/868,987, filed Dec. 23, 1999, Murdin et al.
U.S. Appl. No. 09/471,194, filed Dec. 23, 1999, Murdin et al.
U.S. Appl. No. 09/522,606, filed Mar. 10, 2000, Murdin et al.
U.S. Appl. No. 09/609,243, filed Jun. 30, 2000, Murdin et al.
U.S. Appl. No. 09/662,813, filed Sep. 15, 2000, Murdin et al.
U.S. Appl. No. 09/663,362, filed Sep. 15, 2000, Murdin et al.
U.S. Appl. No. 09/663,360, filed Sep. 15, 2000, Murdin et al.
U.S. Appl. No. 09/663,361, filed Sep. 15, 2000, Murdin et al.
U.S. Appl. No. 09/662,814, filed Sep. 15, 2000, Murdin et al.
U.S. Appl. No. 09/662,812, filed Sep. 15, 2000, Murdin et al.
U.S. Appl. No. 09/709,473, filed Nov. 13, 2000, Murdin et al.
U.S. Appl. No. 09/709,474, filed Nov. 13, 2000, Murdin et al.
U.S. Appl. No. 09/709,384, filed Nov. 13, 2000, Murdin et al.
U.S. Appl. No. 09/747,349, filed Dec. 22, 2000, Murdin et al.
U.S. Appl. No. 09/523,647, filed Mar. 10, 2000, Murdin et al.
Allegra et al.; "Acute Exacerbations of Asthma in Adults: role of *Chlamydia pneumoniae* Infection"; European Respiratory Journal; vol. 7, No. 12; Dec. 1994; pp. 2165-2168.
Arnon et al. FASEB J. Nov. 1992; 6(14): 3265-74.
Attwood et al., Science (2000) 290:471-473.

(Continued)

*Primary Examiner*—Robert B Mondesi
*Assistant Examiner*—Padma V Baskar

(57) ABSTRACT

The present invention provides a method of nucleic acid, including DNA, immunization of a host, including humans, against disease caused by infection by a strain of *Chlamydia*, specifically *C. pneumoniae*, employing a vector containing a nucleotide sequence encoding a 98 kDa outer membrane protein of a strain of *Chlamydia pneumoniae* and a promoter to effect expression of the 98 kDa outer membrane protein gene in the host. Modifications are possible within the scope of this invention.

26 Claims, 20 Drawing Sheets

OTHER PUBLICATIONS

Figure 2A:
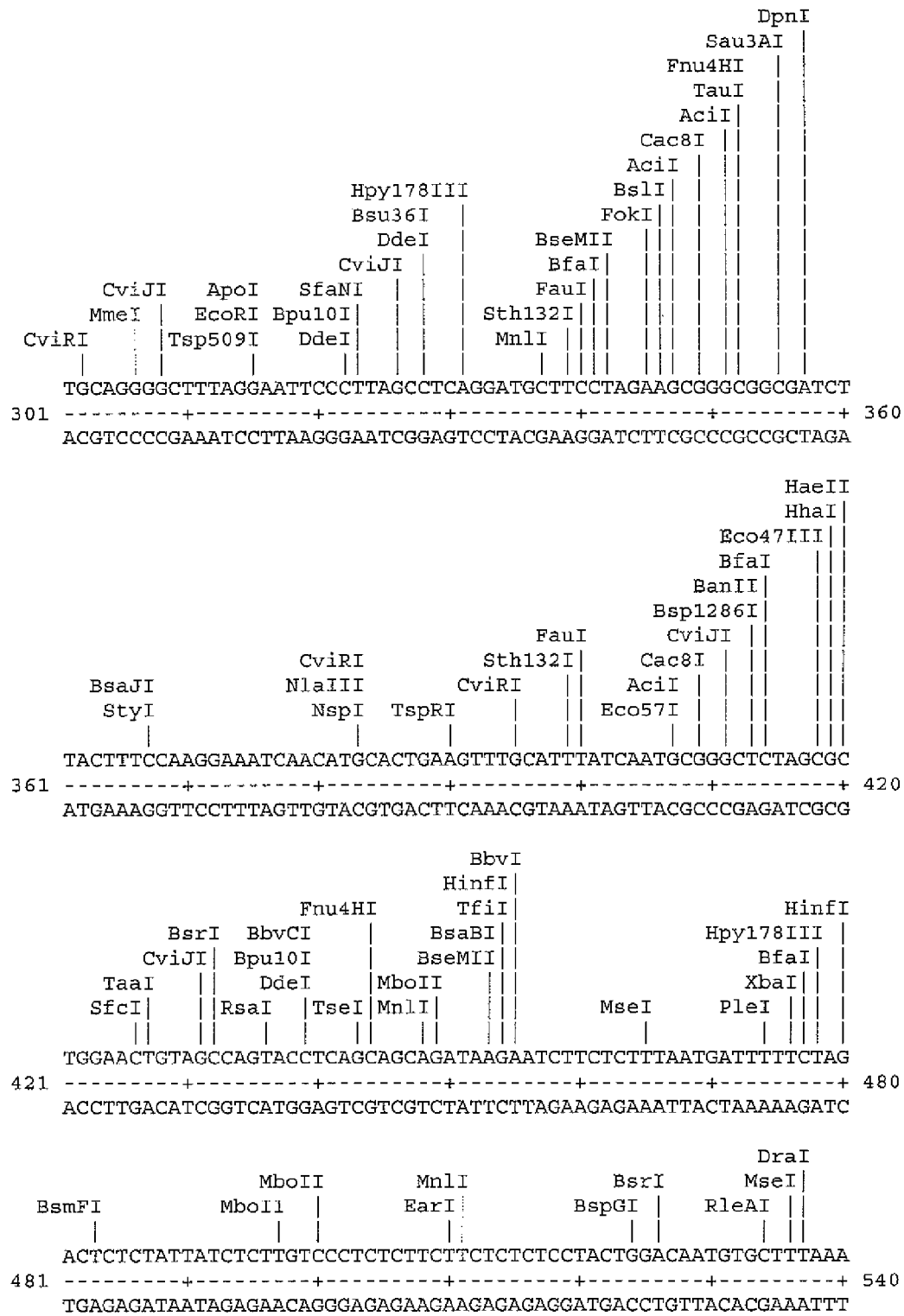

Ausubel et al.; "Current Protocols in Molecular Biology"; John Wiley & Sons Inc.; vol. 1; 1994; 15 sheets.

Bachmaier et al.; "*Chlamydia* Infections and Heart Disease Linked Through Antigenic Minicry"; Science; vol. 283; Feb. 26, 1999; pp. 1335-1339.

Bjornsson et al.; "Serology of *Chlamydia* in relation to Asthma and Bronchial Hyperresponsiveness"; Scand Journal of Infection Diseases; vol. 28, No. 1; 1996; pp. 63-69.

Boselgo et al., Vaccines and Immunotherapy (1991) Chap. 17: Gonorrhea Vaccines, pp. 211-223.

Bowie et al (Science, 1990, 257:1306-1310).

Burgess et al., The Journal of Cell Biology, 111:2129-2138, 1990.

Cagnon et al.; "A New Family of Sugar-Inducible Expression Vectors for *Escherichia coli*"; Protein Engineering; vol. 4, No. 7; 1991; pp. 843-847.

Campbell et al.; "Serological Response to *Chlamydia pneumoniae* Infection"; Journal of Clinical Microbiology; vol. 28, No. 6; Jun. 1990; pp. 1261-1264.

Campbell et al.; "Detection of *Chlamydia pneumoniae* TWAR in Human Coronary Atherectomy Tissues"; The Journal of Infectious Diseases; vol. 172, No. 2; Aug. 1995; pp. 585-588.

Campbell et al.; "Structural and Antigenic Analysis of *Chlamydia pneumoniae*"; Infection and Immunity; vol. 58, No. 1; Jan. 1990; pp. 93-97.

Campos et al. ; "A *Chlamydial* major Outer Membrane Protein Extract as a Trachoma Vaccine Candidate"; Investigation of Ophthalmology and Visual Science; vol. 36, No. 8; Jul. 1995; pp. 1477-1491.

Casey & Davidson; Nucleic Acids Research; vol. 4, No. 5; 1977; pp. 1539-1553.

Cotter et al.; Protective Efficacy of Major Outer Membrane Protein-Specific Immunoglobulin A (IgA) and IgG Monoclonal Antibodies in a Murine Model of *Chlamydia trachomatis* Genital Tract Infection; Infection and Immunity; vol. 63, No. 12; Dec. 1995; pp. 4704-4714.

Chiu et al.; "*Chlamydia pneumoniae*, Cytomegalovirus, and Herpes Simplex Virus in Atherosclerosis of the Carotid Artery"; Circulation; vol. 96, No. 7; Oct. 7, 1997; pp. 2144-2148.

Current Protocols in Immunology, 1997 unit 9.7.5.

Davis et al.; "A Manual for Genetic Engineering: Advanced Bacterial Genetics"; Cold Spring Harbor Laboratory Press; 1980; pp. 174-176. cited by other.

Dion et al.; "Virus Envelope-Based Peptide Vaccines Against Virus-Induced Mammary Tumors"; Virology; vol. 179, No. 1; Nov. 1990; pp. 474-477.

Ellis, Vaccines: New Technologies for Making vaccines (1988), pp. 568-574.

Fong et al.; "Rabbit Model for *Chlamydia pneumoniae* Infection"; Journal of Clinical Microbiology; vol. 15, No. 1; Jan. 1997; pp. 48-52.

Gaydos et al.; "Similarity of *Chlamydia pneumoniae* Strains in the Variable Domain IV Region of the Major Outer Membrane Protein Gene"; Infection and Immunity; vol. 60, No. 12; Dec. 1992; pp. 5319;5323.

Grayston et al.; "Evidence that *Chlamydia pneumoniae* Causes Pneumonia and Bronchitis"; The Journal of Infectious Diseases; vol. 168, No. 5; Nov. 1995; pp. 1231-1235.

Grayston et al.; "A New Respiratory Tract Pathogen: *Chlamydia pneumoniae* Strain TWAR"; The Journal of Infectious Diseases; vol. 161, No. 4; Apr. 1990; pp. 618-625.

Hahn; "Treatment of *Chlamydia pneumoniae* Infection in Adult Asthma: A Before-After Trial"; J. Fam. Pract. vol. 41, No. 4; Oct. 1995; pp. 345-351.

Hahn et al.; "Association of *Chlamydia pneumoniae* (Strain TWAR) Infection With Wheezing, Asthmatic Bronchitis, and Adult-Onset Asthma"; The Journal of the American Medical Association; vol. 266, No. 2; Jul. 10, 1991; pp. 225-230.

Hahn et al.; "Evidence for *Chlamydia pneumoniae* Infection in Steroid-Dependent Asthma"; Ann Allergy Asthma Immunology; vol. 80, No. 1, Jan. 1998; pp. 45-49.

Hahn et al.; "Association of *Chlamydia pneumoniae* IgA Antibodies With Recently Symptomatic Asthma"; Epidemiology Infection; vol. 117, No. 3; Dec. 1996; pp. 513-517.

Herbert et al The Dictionary of Immunology, Academic Press, 3rd Edition, London, 1985, pp. 58-59.

Holmes Exp. Opin. Invest. Drugs, 2001, 10(3):511-519.

Hughes et al.; "Synthetic Peptides Representing Epitopes of Outer Membrane Protein F of *Pseudomonas aeruginosa* That Elicit Antibodies Reactive With Whole Cells of Heterologous Immunotype Strains of *P. aeruginosa*"; Infection and Immunity; vol. 60, No. 9, Sep. 1992; pp. 3497-3503.

Igietseme et al.; "Resolution of Murine *Chlamydial* Genital Infection by the Adoptive Transfer of a Biovar-Specific, TH, Lymphocyte Clone"; Regional Immunology; vol. 5; 1993; pp. 317-324.

Iijima et al.; "Characterization of *Chlamydia pneumoniae* Species-Specific Proteins Immunodominant in Humans"; Journal of clinical Microbiology; vol. 32, No. 3; Mar. 1994; pp. 583-588.

Jackson et al.; K121; 36.sup.th ICAAC; Sep. 15-18, 1996; p. 272; Abstract.

Jobling et al. (Mol. Microbiol. 1991, 5(7): 1755-67.

Jones et al.; "Efficacy Trials With Tissue-Culture Grown, Inactivated Vaccines Against *Chlamydial* Abortion in Sheep"; Vaccine; vol. 13, No. 8; 1995; pp. 715-723.

Kalman et al., "Comparative Genomes of *Chlamydia pneumoniae* and *C. trachomatis*," Nature Genetics, vol. 21, Apr. 1999, pp. 385-389.

Kunkel; "Rapid and Efficient Site-Specific Mutagenesis Without Phenotypic Selection"; National Academy of Sciences Proceedings; vol. 82; Jan. 1985; pp. 488-492.

Kuo et al.; "Demonstration of *Chlamydia pneumoniae* in Atherosclerotic Lesions of Coronary Arteries"; The Journal of Infectious Diseases; vol. 167, No. 4; Apr. 1993; pp. 841-849.

Kuo et al.; "Detection of *Chlamydia pneumoniae* in Aortic Lesions of Atherosclerosis by Immunocytochemical Stain"; Arteriosclerosis and Thrombosis; vol. 13, No. 10; Oct. 1993; pp. 1501-1504.

Landers et al.; "Role of L3T4-Bearing T-Cell Populations in Experimental Murine *Chlamydial salpingitis*" Infection and Immunity; vol. 59; No. 10; Oct. 1991; pp. 3774-3777.

Langeveld et al; "Effective Induction of Neutralizing Antibodies With the Amino Terminus of VP2 of Canine Parvovirus as a Synthetic Peptide"; Vaccine; vol. 12, No. 15; 1994; pp. 1473-1480.

Lazar et al., Molecular and Cellular Biology, 8(3): 1247-1252, 1988.

Longbottom et al., EMBL U72499; (Feb. 1, 1997), AAB18188.1.

Linnanmaki et al.; "*Chlamydia pneumoniae*-Specific Circulating Immune Complexes in Patients With Chronic Coronary Heart Disease"; Circulation; vol. 87, No. 4; Apr. 1993; pp. 1130-1134.

Magee et al.; "*Chlamydia trachomatis* Pneumonia in the Severe Combined Irmnunodeficicncy (SCID) Mouse"; Regional Immunology; vol. 5; 1993; pp. 305-311.

Magee et al.; "role of CDS T Cells in Primary *Chlamydia* Infection"; Infection and Immunity; vol. 63, No. 2; Feb. 1995; pp. 516-521.

Marrie; "Community-Acquired Pneumonia"; Clinical Infectious Diseases; vol. 18, No. 4; Apr. 1993; pp. 501-515.

McCafferty et al.; "Electrophoretic Analysis of the Major Outer Membrane Protein of *Chlamydia psittaci* Reveals Multimers Which Are Recognized by Protective Monoclonal Antibodies"; Infection and Immunity; vol. 63, No. 6; Jun. 1995; pp. 2387-2389.

Melnick et al.; "Past Infection by *Chlamydia pneumoniae* Strain TWAR and Asymptomatic Carotid Atherosclerosis"; American Journal of Medicine; vol. 95; Nov. 1993; pp. 499-504.

Niman, Proc. Natl. Acad. Sci., USA 1983, vol. 80, 4949-4953.

Pal et al.; "Intranasal Immunization Induces Long-Term Protection in Mice Against a *Chlamydia trachomatis* Genital Challenge"; Infection and Immunity; vol. 64, No. 12; Dec. 1996; pp. 5341-5348.

Perez Melgosa et al.; "Outer Membrane Complex Proteins of *Chlamydia pneumoniae*"; FEMS Microbiology Letters; vol. 112, No. 2; Sep. 1993; pp. 199-204.

Perez Megosa et al.; "Isolation and Characterization of a Gene Encoding a *Chlamydia pneumoniae* 76-Kilodalton Protein Containing A Species-Specific Epitope"; Infection and Immunity; vol. 62, No. 3; Mar. 1994; pp. 880-886.

Ramirez et al.; "Isolation of *Chlamydia pneumoniae* From the Coronary Artery of a Patient With Coronary Atherosclerosis"; Annals of Internal Medicine; vol. 125, No. 12; Dec. 15, 1996; pp. 979-982.

Reece et al. J. Immunol. 1994, vol. 172, p. 241.

Roitt et al Immunology, 1993, Mosby, St. Louis, p. 7.7-7.8.

Rudinger et al, in "Peptide Hormones", edited by Parsons, J.A., University Park Press, Jun. 1976, p. 1-6.
Russell et al., J. Mol. Bio.(1994), 244, pp. 332-350.
Saikku et al.; "Chronic *Chlamydia pneumoniae* Infection as a Risk Factor for Coronary Heart Disease in the Helsinki Heart Study"; Annals of Internal Medicine; vol. 116, No. 4; Feb. 15, 1992; pp. 273-278.
Saikku et al.; The Lancet; vol. II, No. 8618; Oct. 1988; pp. 983-985.
Shor et al.; "Detection of *Chlamydia pneumoniae* in Coronary Arterial Fatty Streaks and Atheromatous Plaques"; South African Medical Journal; vol. 82; Sep. 1992; pp. 158-161.
Silhavy et al.; "Experiments with Gene Fusions"; Cold Spring Harbor Laboratory Press; 1994; pp. 191-195.
Skolnick et al., Trends in Biotech. (2000), 18(1), pp. 34-39.
Snijders et al.; "Identification of Linear Epitopes on Semliki Forest Virus E2 Membrane Protein and Their Effectiveness as a Synthetic Peptide Vaccine"; The Journal of General Virology; vol. 72, No. 3; Mar. 1991; pp. 557-565.
Stephens et al., "Genome Sequence of an Obligate Intracellular Pathogen of Humans: *Chlamydia trachomatis*," Oct. 23, 1998, vol. 282, Science, pp. 754-759.
Taber's Cyclopedic Medical Dictionary, FA Davis, Philadelphia, 16th Ed., 1985.

Takase et al.; "Genes Encoding Two Lipoproteins in the IeuS-dacA Region of the *Escherichia coli*Chromosome"; Journal of Bacteriology; vol. 169, No. 12; Dec. 1987; pp. 5692-5699.
Thom et al.; "Association of Prior Infection With *Chlamydia pneumoniae* and Angiographically Demonstrated Coronary Artery Disease"; The Journal of the American Medical Association; vol. 268, No. 1; Jul. 1, 1992; pp. 68-72.
Wang et al.; "Microimmunofluorescence Serological Studies With the TWAR Organism"; *Chlamydial* Infections; 1986; pp. 329-333.
Watson et al.; The nucleotide Sequence of the 60kDa Cysteine Rich Outer Membrane Protein of *Chlamydia pneumoniae* Strain; Nucleic Acids Research; vol. 18, No. 17; Sep 11, 1990; p. 5299.
Watson et al.; "The CrP Operon of *Chlamydia psittaci* and *Chlamydia pneumoniae*"; Microbiology; vol. 141, No. 10; Oct. 1995; pp. 2489-2497.
Wiedmann-Al-Ahmad et al.; "Reactions of Polyclonal and Neutralizing Anti-p54 Monoclonal Antibodies With An Isolated, species-Specific 54-Kilodalton Protein of *Chlamydia pneumoniae*"; Clinical and Diagnostic Laboratory Immunology; vol. 4, No. 6; Nov. 1997; pp. 700-704.

* cited by examiner

Figure 1: Nucleotide and amino acid sequences of CPN100640

```
gattctccgc atcaatcaat tccttgcgtt tcccttgatt tctttttttc tttacagtat   60
ttgctaattt aatttccttg tttcaaaaaa gtgcttacaa atg aag tcc tct gtc    115
                                              Met Lys Ser Ser Val
                                               1               5 tct tgg ttg ttc ttt tct tca atc ccg ctc ttt tca tcg ctc tct ata    163
Ser Trp Leu Phe Phe Ser Ser Ile Pro Leu Phe Ser Ser Leu Ser Ile
                    10              15                  20 gtc gcg gca gag gtg acc tta gat agc agc aat aat agc tat gat gga    211
Val Ala Ala Glu Val Thr Leu Asp Ser Ser Asn Asn Ser Tyr Asp Gly
                25                  30                  35 tct aac gga act acc ttc acg gtc ttt tcc act acg gac gct gct gca    259
Ser Asn Gly Thr Thr Phe Thr Val Phe Ser Thr Thr Asp Ala Ala Ala
            40                  45                  50 gga act acc tat tcc tta ctt tcc gac gta tcc ttt caa aat gca ggg    307
Gly Thr Thr Tyr Ser Leu Leu Ser Asp Val Ser Phe Gln Asn Ala Gly
        55                  60                  65 gct tta gga att ccc tta gcc tca gga tgc ttc cta gaa gcg ggc ggc    355
Ala Leu Gly Ile Pro Leu Ala Ser Gly Cys Phe Leu Glu Ala Gly Gly
 70                  75                  80                  85 gat ctt act ttc caa gga aat caa cat gca ctg aag ttt gca ttt atc    403
Asp Leu Thr Phe Gln Gly Asn Gln His Ala Leu Lys Phe Ala Phe Ile
                90                  95                 100 aat gcg ggc tct agc gct gga act gta gcc agt acc tca gca gca gat    451
Asn Ala Gly Ser Ser Ala Gly Thr Val Ala Ser Thr Ser Ala Ala Asp
            105                 110                 115 aag aat ctt ctc ttt aat gat ttt tct aga ctc tct att atc tct tgt    499
Lys Asn Leu Leu Phe Asn Asp Phe Ser Arg Leu Ser Ile Ile Ser Cys
        120                 125                 130 ccc tct ctt ctt ctc tct cct act gga caa tgt gct tta aaa tct gtg    547
Pro Ser Leu Leu Leu Ser Pro Thr Gly Gln Cys Ala Leu Lys Ser Val
    135                 140                 145
```

Figure 1A

| | | | | | | | | | | | | | | | |
|---|---|---|---|---|---|---|---|---|---|---|---|---|---|---|---|
|ggg|aat|cta|tct|cta|act|ggc|aat|tcc|caa|att|ata|ttt|act|cag|aac| 595
|Gly|Asn|Leu|Ser|Leu|Thr|Gly|Asn|Ser|Gln|Ile|Ile|Phe|Thr|Gln|Asn|
|Gly|Asn|Leu|Ser|Leu|Thr|Gly|Asn|Ser|Gln|Ile|Ile|Phe|Thr|Gln|Asn|
|150| | | | |155| | | |160| | | | |165| |

```
ggg aat cta tct cta act ggc aat tcc caa att ata ttt act cag aac    595
Gly Asn Leu Ser Leu Thr Gly Asn Ser Gln Ile Ile Phe Thr Gln Asn
Gly Asn Leu Ser Leu Thr Gly Asn Ser Gln Ile Ile Phe Thr Gln Asn
150                 155             160                 165 ttc tcg tca gat aac ggc ggt gtt atc aat acg aaa aac ttc tta tta    643
Phe Ser Ser Asp Asn Gly Gly Val Ile Asn Thr Lys Asn Phe Leu Leu
Phe Ser Ser Asp Asn Gly Gly Val Ile Asn Thr Lys Asn Phe Leu Leu
                170             175                 180 tca ggg aca tct cag ttt gcg agc ttt tcg aga aac caa gcc ttc aca    691
Ser Gly Thr Ser Gln Phe Ala Ser Phe Ser Arg Asn Gln Ala Phe Thr
Ser Gly Thr Ser Gln Phe Ala Ser Phe Ser Arg Asn Gln Ala Phe Thr
            185                 190                 195 ggg aag caa ggc ggt gta gtt tac gct aca gga act ata act atc gag    739
Gly Lys Gln Gly Gly Val Val Tyr Ala Thr Gly Thr Ile Thr Ile Glu
Gly Lys Gln Gly Gly Val Val Tyr Ala Thr Gly Thr Ile Thr Ile Glu
        200                 205                 210 aac agc cct ggg ata gtt tcc ttc tct caa aac cta gcg aaa gga tct    787
Asn Ser Pro Gly Ile Val Ser Phe Ser Gln Asn Leu Ala Lys Gly Ser
Asn Ser Pro Gly Ile Val Ser Phe Ser Gln Asn Leu Ala Lys Gly Ser
    215                 220                 225 ggc ggt gct ctg tac agc act gac aac tgt tcg att aca gat aac ttt    835
Gly Gly Ala Leu Tyr Ser Thr Asp Asn Cys Ser Ile Thr Asp Asn Phe
Gly Gly Ala Leu Tyr Ser Thr Asp Asn Cys Ser Ile Thr Asp Asn Phe
230                 235                 240                 245 caa gtg atc ttt gac ggc aat agt gct tgg gaa gcc gct caa gct cag    883
Gln Val Ile Phe Asp Gly Asn Ser Ala Trp Glu Ala Ala Gln Ala Gln
Gln Val Ile Phe Asp Gly Asn Ser Ala Trp Glu Ala Ala Gln Ala Gln
            250                 255                 260 ggc ggg gct att tgt tgc act acg aca gat aaa aca gtg act ctt act    931
Gly Gly Ala Ile Cys Cys Thr Thr Thr Asp Lys Thr Val Thr Leu Thr
Gly Gly Ala Ile Cys Cys Thr Thr Thr Asp Lys Thr Val Thr Leu Thr
        265                 270                 275 ggg aac aaa aac ctc tct ttc aca aat aat aca gca ttg aca tat ggc    979
Gly Asn Lys Asn Leu Ser Phe Thr Asn Asn Thr Ala Leu Thr Tyr Gly
Gly Asn Lys Asn Leu Ser Phe Thr Asn Asn Thr Ala Leu Thr Tyr Gly
    280                 285                 290 gga gcc atc tct gga ctc aag gtc agt att tcc gct gga ggt cct act    1027
Gly Ala Ile Ser Gly Leu Lys Val Ser Ile Ser Ala Gly Gly Pro Thr
Gly Ala Ile Ser Gly Leu Lys Val Ser Ile Ser Ala Gly Gly Pro Thr
295                 300                 305 cta ttt caa agt aat atc tca gga agt agc gcc ggt cag gga gga gga    1075
Leu Phe Gln Ser Asn Ile Ser Gly Ser Ser Ala Gly Gln Gly Gly Gly
Leu Phe Gln Ser Asn Ile Ser Gly Ser Ser Ala Gly Gln Gly Gly Gly
310                 315                 320                 325
```

Figure 1B

```
gga gcg atc aat ata gca tct gct ggg gaa ctc gct ctc tct gct act      1123
Gly Ala Ile Asn Ile Ala Ser Ala Gly Glu Leu Ala Leu Ser Ala Thr
Gly Ala Ile Asn Ile Ala Ser Ala Gly Glu Leu Ala Leu Ser Ala Thr
            330                 335                 340 tct gga gat att acc ttc aat aac aac caa gtc acc aac gga agc aca      1171
Ser Gly Asp Ile Thr Phe Asn Asn Asn Gln Val Thr Asn Gly Ser Thr
Ser Gly Asp Ile Thr Phe Asn Asn Asn Gln Val Thr Asn Gly Ser Thr
            345                 350                 355 agt aca aga aac gca ata aat atc att gat acc gct aaa gtc aca tcg      1219
Ser Thr Arg Asn Ala Ile Asn Ile Ile Asp Thr Ala Lys Val Thr Ser
Ser Thr Arg Asn Ala Ile Asn Ile Ile Asp Thr Ala Lys Val Thr Ser
            360                 365                 370 ata cga gct gct acg ggg caa tct atc tat ttc tat gat ccc atc aca      1267
Ile Arg Ala Ala Thr Gly Gln Ser Ile Tyr Phe Tyr Asp Pro Ile Thr
Ile Arg Ala Ala Thr Gly Gln Ser Ile Tyr Phe Tyr Asp Pro Ile Thr
    375                 380                 385 aat cca gga acc gca gct tct acc gac aca ttg aac tta aac tta gca      1315
Asn Pro Gly Thr Ala Ala Ser Thr Asp Thr Leu Asn Leu Asn Leu Ala
Asn Pro Gly Thr Ala Ala Ser Thr Asp Thr Leu Asn Leu Asn Leu Ala
390                 395                 400                 405 gat gcg aac agt gag atc gag tat ggg ggt gcg att gtc ttt tct gga      1363
Asp Ala Asn Ser Glu Ile Glu Tyr Gly Gly Ala Ile Val Phe Ser Gly
Asp Ala Asn Ser Glu Ile Glu Tyr Gly Gly Ala Ile Val Phe Ser Gly
            410                 415                 420 gaa aag ctt tcc cct aca gaa aaa gca atc gct gca aac gtc acc tct      1411
Glu Lys Leu Ser Pro Thr Glu Lys Ala Ile Ala Ala Asn Val Thr Ser
Glu Lys Leu Ser Pro Thr Glu Lys Ala Ile Ala Ala Asn Val Thr Ser
            425                 430                 435 act atc cga caa cct gca gta tta gcg cgg gga gat ctt gta ctt cgt      1459
Thr Ile Arg Gln Pro Ala Val Leu Ala Arg Gly Asp Leu Val Leu Arg
Thr Ile Arg Gln Pro Ala Val Leu Ala Arg Gly Asp Leu Val Leu Arg
            440                 445                 450 gat gga gtc acc gta act ttc aag gat ctg act caa agt cca gga tcc      1507
Asp Gly Val Thr Val Thr Phe Lys Asp Leu Thr Gln Ser Pro Gly Ser
Asp Gly Val Thr Val Thr Phe Lys Asp Leu Thr Gln Ser Pro Gly Ser
            455                 460                 465 cgc atc tta atg gat ggg ggg act aca ctt agt gct aaa gag gca aat      1555
Arg Ile Leu Met Asp Gly Gly Thr Thr Leu Ser Ala Lys Glu Ala Asn
Arg Ile Leu Met Asp Gly Gly Thr Thr Leu Ser Ala Lys Glu Ala Asn
470                 475                 480                 485
```

Figure 1C

```
ctt tcg ctt aat ggc tta gca gta aat ctc tcc tct tta gat gga acc     1603
Leu Ser Leu Asn Gly Leu Ala Val Asn Leu Ser Ser Leu Asp Gly Thr
Leu Ser Leu Asn Gly Leu Ala Val Asn Leu Ser Ser Leu Asp Gly Thr
                490                 495                 500 aac aag gca gct tta aaa aca gaa gct gca gat aaa aat atc agc cta     1651
Asn Lys Ala Ala Leu Lys Thr Glu Ala Ala Asp Lys Asn Ile Ser Leu
Asn Lys Ala Ala Leu Lys Thr Glu Ala Ala Asp Lys Asn Ile Ser Leu
            505                 510                 515 tcg gga acg att gcg ctt att gac acg gaa ggg tca ttc tat gag aat     1699
Ser Gly Thr Ile Ala Leu Ile Asp Thr Glu Gly Ser Phe Tyr Glu Asn
Ser Gly Thr Ile Ala Leu Ile Asp Thr Glu Gly Ser Phe Tyr Glu Asn
        520                 525                 530 cat aac tta aaa agt gct agt acc tat cct ctt ctt gaa ctt acc acc     1747
His Asn Leu Lys Ser Ala Ser Thr Tyr Pro Leu Leu Glu Leu Thr Thr
His Asn Leu Lys Ser Ala Ser Thr Tyr Pro Leu Leu Glu Leu Thr Thr
    535                 540                 545 gca gga gcc aac gga acg att act ctg gga gct ctt tct acc ctg act     1795
Ala Gly Ala Asn Gly Thr Ile Thr Leu Gly Ala Leu Ser Thr Leu Thr
Ala Gly Ala Asn Gly Thr Ile Thr Leu Gly Ala Leu Ser Thr Leu Thr
550                 555                 560                 565 ctt caa gaa cct gaa acc cac tac ggg tat caa gga aac tgg cag ttg     1843
Leu Gln Glu Pro Glu Thr His Tyr Gly Tyr Gln Gly Asn Trp Gln Leu
Leu Gln Glu Pro Glu Thr His Tyr Gly Tyr Gln Gly Asn Trp Gln Leu
                570                 575                 580 tct tgg gca aat gca aca tcc tca aaa ata gga agc atc aac tgg acc     1891
Ser Trp Ala Asn Ala Thr Ser Ser Lys Ile Gly Ser Ile Asn Trp Thr
Ser Trp Ala Asn Ala Thr Ser Ser Lys Ile Gly Ser Ile Asn Trp Thr
            585                 590                 595 cgt aca gga tac att cct agt cct gag aga aaa agt aat ctc cct cta     1939
Arg Thr Gly Tyr Ile Pro Ser Pro Glu Arg Lys Ser Asn Leu Pro Leu
Arg Thr Gly Tyr Ile Pro Ser Pro Glu Arg Lys Ser Asn Leu Pro Leu
        600                 605                 610 aat agc tta tgg gga aac ttt ata gat ata cgc tcg atc aat cag ctt     1987
Asn Ser Leu Trp Gly Asn Phe Ile Asp Ile Arg Ser Ile Asn Gln Leu
Asn Ser Leu Trp Gly Asn Phe Ile Asp Ile Arg Ser Ile Asn Gln Leu
    615                 620                 625 ata gaa acc aag tcc agt ggg gag cct ttt gag cgt gag cta tgg ctt     2035
Ile Glu Thr Lys Ser Ser Gly Glu Pro Phe Glu Arg Glu Leu Trp Leu
Ile Glu Thr Lys Ser Ser Gly Glu Pro Phe Glu Arg Glu Leu Trp Leu
630                 635                 640                 645 tca gga att gcg aat ttc ttc tat aga gat tct atg ccc acc cgc cat     2083
Ser Gly Ile Ala Asn Phe Phe Tyr Arg Asp Ser Met Pro Thr Arg His
Ser Gly Ile Ala Asn Phe Phe Tyr Arg Asp Ser Met Pro Thr Arg His
                650                 655                 660
```

Figure 1D

```
ggt ttc cgc cat atc agc ggg ggt tat gca cta ggg atc aca gca aca    2131
Gly Phe Arg His Ile Ser Gly Gly Tyr Ala Leu Gly Ile Thr Ala Thr
Gly Phe Arg His Ile Ser Gly Gly Tyr Ala Leu Gly Ile Thr Ala Thr
            665                 670                 675 act cct gcc gag gat cag ctt act ttt gcc ttc tgc cag ctc ttt gct    2179
Thr Pro Ala Glu Asp Gln Leu Thr Phe Ala Phe Cys Gln Leu Phe Ala
Thr Pro Ala Glu Asp Gln Leu Thr Phe Ala Phe Cys Gln Leu Phe Ala
            680                 685                 690 aga gat cgc aat cat att aca ggt aag aac cac gga gat act tac ggt    2227
Arg Asp Arg Asn His Ile Thr Gly Lys Asn His Gly Asp Thr Tyr Gly
Arg Asp Arg Asn His Ile Thr Gly Lys Asn His Gly Asp Thr Tyr Gly
            695                 700                 705 gcc tct ttg tat ttc cac cat aca gaa ggg ctc ttc gac atc gcc aat    2275
Ala Ser Leu Tyr Phe His His Thr Glu Gly Leu Phe Asp Ile Ala Asn
Ala Ser Leu Tyr Phe His His Thr Glu Gly Leu Phe Asp Ile Ala Asn
710                 715                 720                 725 ttc ctc tgg gga aaa gca acc cga gct ccc tgg gtg ctc tct gag atc    2323
Phe Leu Trp Gly Lys Ala Thr Arg Ala Pro Trp Val Leu Ser Glu Ile
Phe Leu Trp Gly Lys Ala Thr Arg Ala Pro Trp Val Leu Ser Glu Ile
            730                 735                 740 tcc cag atc att cct tta tcg ttc gat gct aaa ttc agt tat ctc cat    2371
Ser Gln Ile Ile Pro Leu Ser Phe Asp Ala Lys Phe Ser Tyr Leu His
Ser Gln Ile Ile Pro Leu Ser Phe Asp Ala Lys Phe Ser Tyr Leu His
            745                 750                 755 aca gac aac cac atg aag aca tat tat acc gat aac tct atc atc aag    2419
Thr Asp Asn His Met Lys Thr Tyr Tyr Thr Asp Asn Ser Ile Ile Lys
Thr Asp Asn His Met Lys Thr Tyr Tyr Thr Asp Asn Ser Ile Ile Lys
            760                 765                 770 ggt tct tgg aga aac gat gcc ttc tgt gca gat ctt gga gct agc ctg    2467
Gly Ser Trp Arg Asn Asp Ala Phe Cys Ala Asp Leu Gly Ala Ser Leu
Gly Ser Trp Arg Asn Asp Ala Phe Cys Ala Asp Leu Gly Ala Ser Leu
            775                 780                 785 cct ttt gtt att tcc gtt ccg tat ctt ctg aaa gaa gtc gaa cct ttt    2515
Pro Phe Val Ile Ser Val Pro Tyr Leu Leu Lys Glu Val Glu Pro Phe
Pro Phe Val Ile Ser Val Pro Tyr Leu Leu Lys Glu Val Glu Pro Phe
790                 795                 800                 805 gtc aaa gta cag tat atc tat gcg cat cag caa gac ttc tac gag cgt    2563
Val Lys Val Gln Tyr Ile Tyr Ala His Gln Gln Asp Phe Tyr Glu Arg
Val Lys Val Gln Tyr Ile Tyr Ala His Gln Gln Asp Phe Tyr Glu Arg
            810                 815                 820
```

Figure 1E

```
cat gct gaa gga cgc gct ttc aat aaa agc gag ctt atc aac gta gag    2611
His Ala Glu Gly Arg Ala Phe Asn Lys Ser Glu Leu Ile Asn Val Glu
His Ala Glu Gly Arg Ala Phe Asn Lys Ser Glu Leu Ile Asn Val Glu
            825                 830                 835 att cct ata ggc gtc acc ttc gaa aga gac tca aaa tca gaa aag gga    2659
Ile Pro Ile Gly Val Thr Phe Glu Arg Asp Ser Lys Ser Glu Lys Gly
Ile Pro Ile Gly Val Thr Phe Glu Arg Asp Ser Lys Ser Glu Lys Gly
            840                 845                 850 act tac gat ctt act ctt atg tat ata ctc gat gct tac cga cgc aat    2707
Thr Tyr Asp Leu Thr Leu Met Tyr Ile Leu Asp Ala Tyr Arg Arg Asn
Thr Tyr Asp Leu Thr Leu Met Tyr Ile Leu Asp Ala Tyr Arg Arg Asn
            855                 860                 865 cct aaa tgt caa act tcc cta ata gct agc gat gct aac tgg atg gcc    2755
Pro Lys Cys Gln Thr Ser Leu Ile Ala Ser Asp Ala Asn Trp Met Ala
Pro Lys Cys Gln Thr Ser Leu Ile Ala Ser Asp Ala Asn Trp Met Ala
870                 875                 880                 885 tat ggt acc aac ctc gca cga caa ggt ttt tct gtt cgt gct gcg aac    2803
Tyr Gly Thr Asn Leu Ala Arg Gln Gly Phe Ser Val Arg Ala Ala Asn
Tyr Gly Thr Asn Leu Ala Arg Gln Gly Phe Ser Val Arg Ala Ala Asn
            890                 895                 900 cat ttc caa gtg aac ccc cac atg gaa atc ttc ggt caa ttc gct ttt    2851
His Phe Gln Val Asn Pro His Met Glu Ile Phe Gly Gln Phe Ala Phe
His Phe Gln Val Asn Pro His Met Glu Ile Phe Gly Gln Phe Ala Phe
            905                 910                 915 gaa gta cga agt tct tca cga aat tat aat aca aac cta ggc tct aag    2899
Glu Val Arg Ser Ser Ser Arg Asn Tyr Asn Thr Asn Leu Gly Ser Lys
Glu Val Arg Ser Ser Ser Arg Asn Tyr Asn Thr Asn Leu Gly Ser Lys
            920                 925                 930 ttt tgt ttc tagattatcg aaaacgtgtt aattaattga acccaagcat            2948
Phe Cys Phe
Phe Cys Phe
    935 ctttctatga aaatacccct gcacaaactc ctgatctctt cgactcttgt cactcccatt 3008 ctattgagca ttgcaactta cggagcagat gcttctttat cc                    3050
```

Figure 2D:
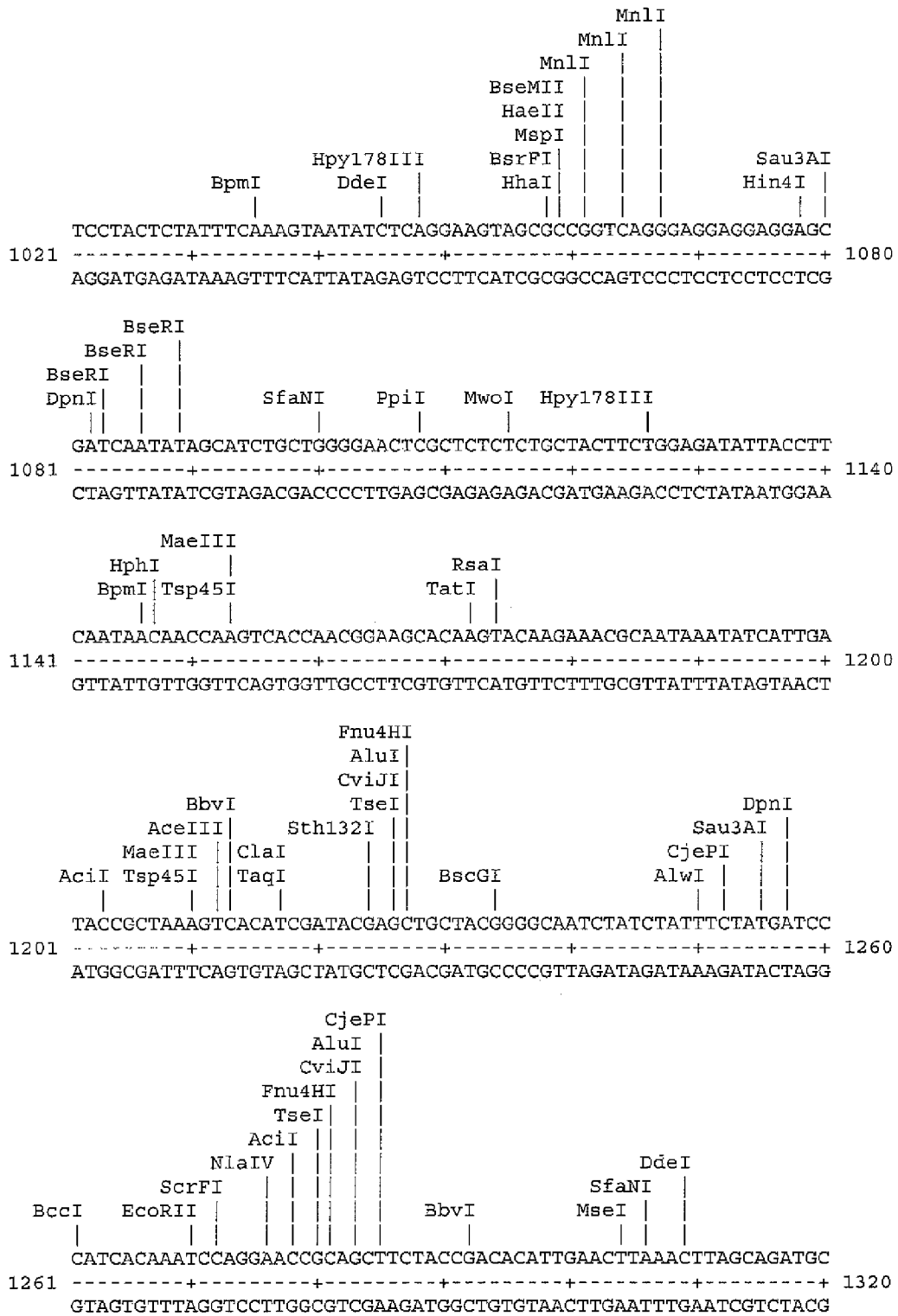
Figure 2E:
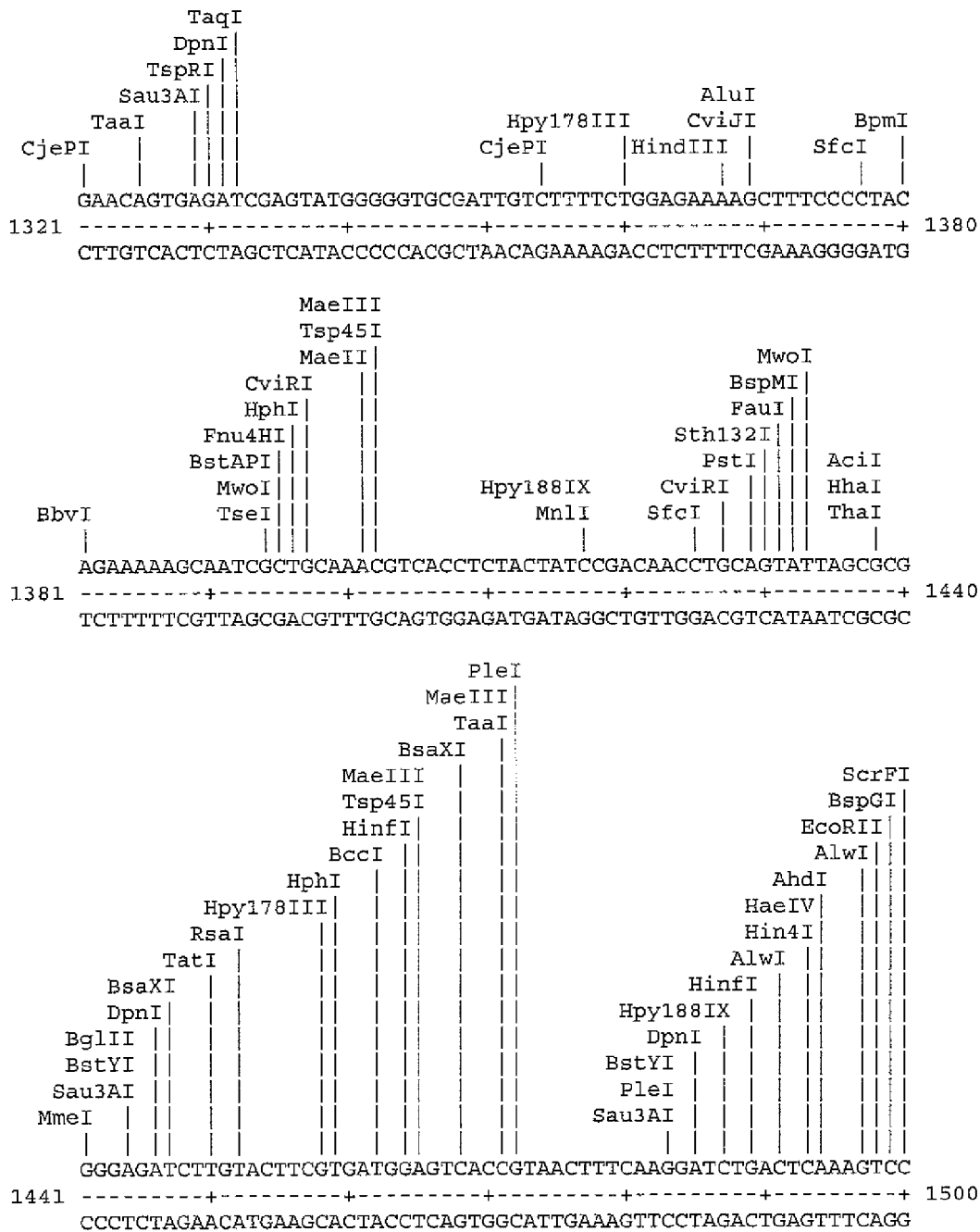
Figure 2F:
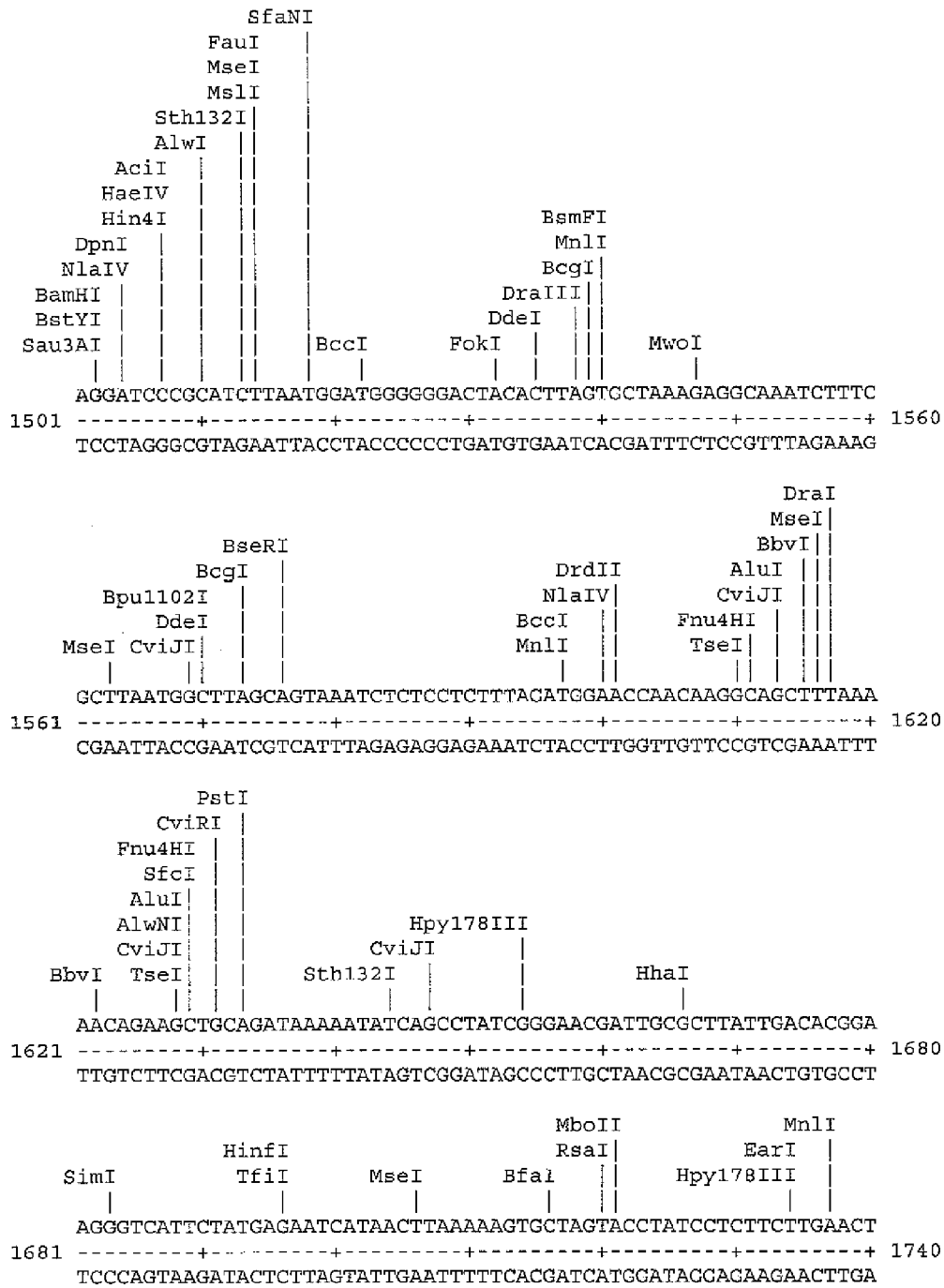
Figure 2G:
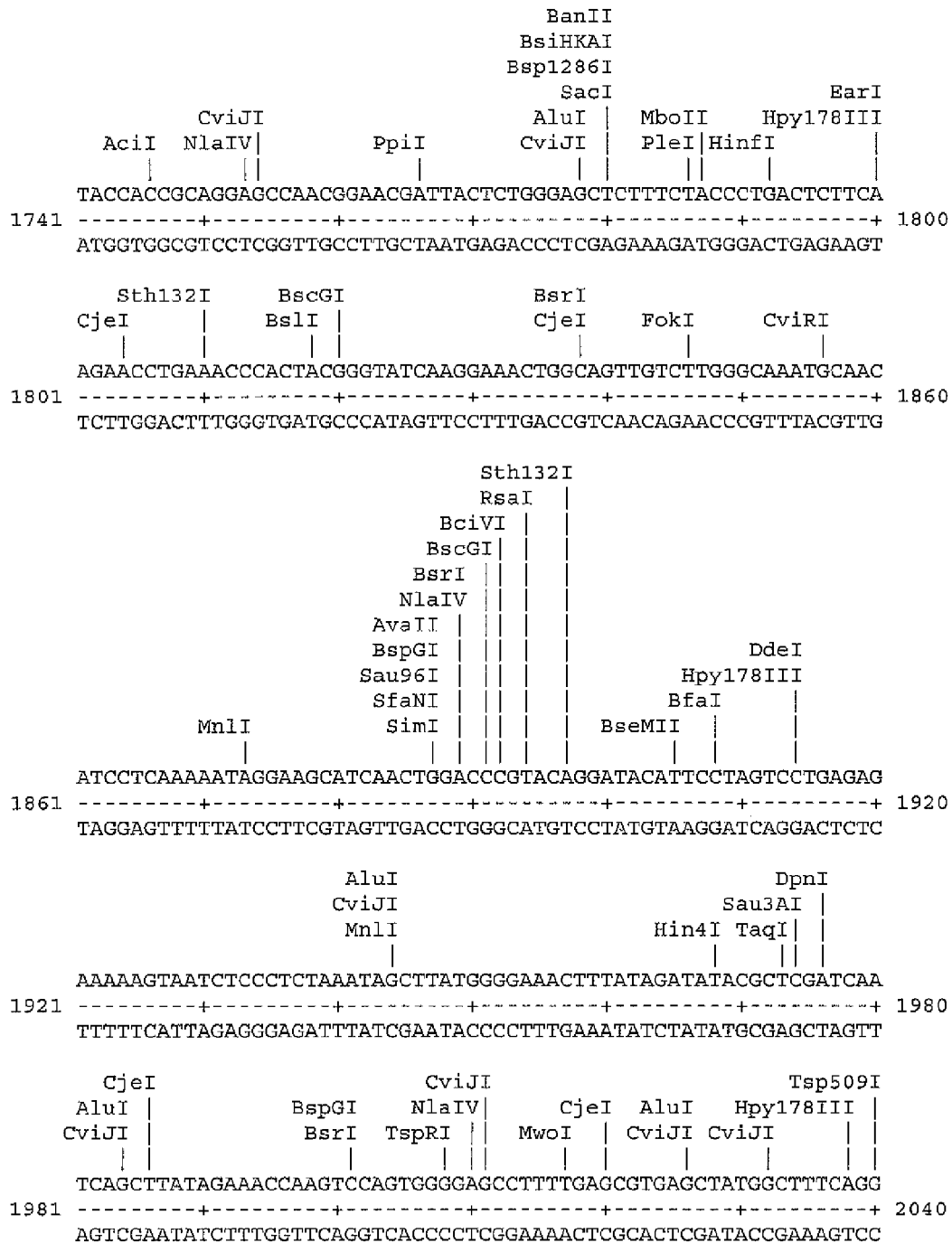
Figure 2I:
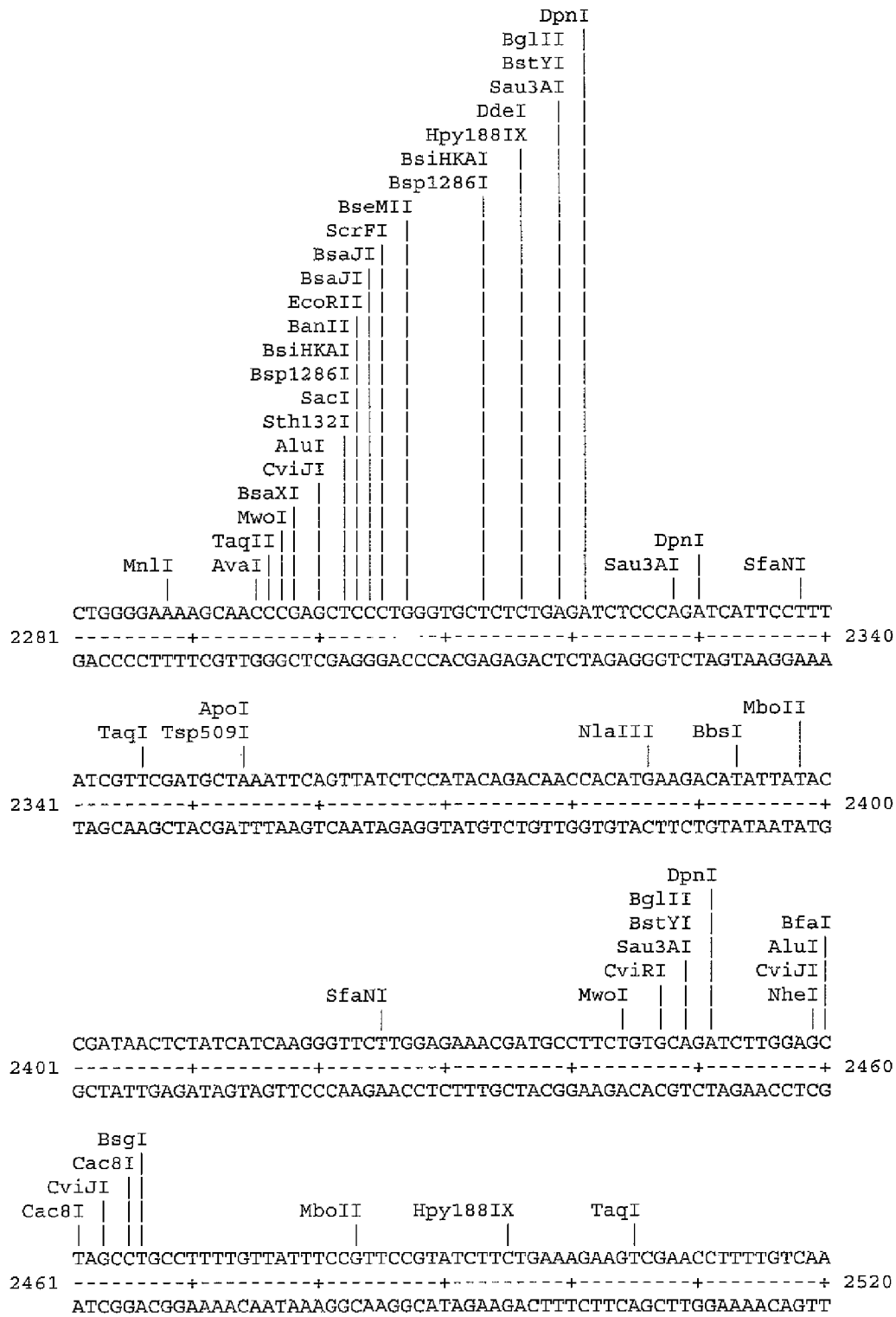
Figure 2J:
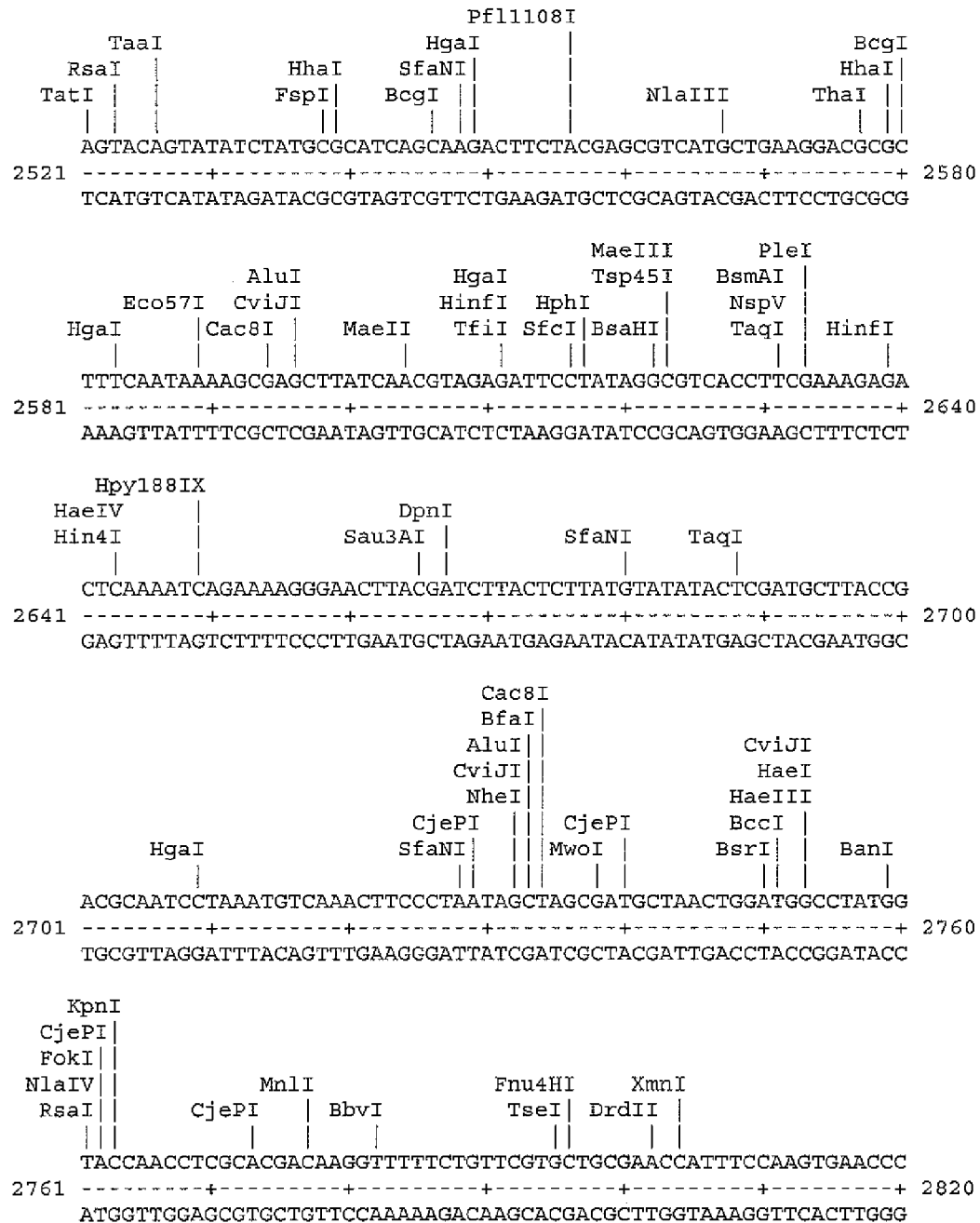

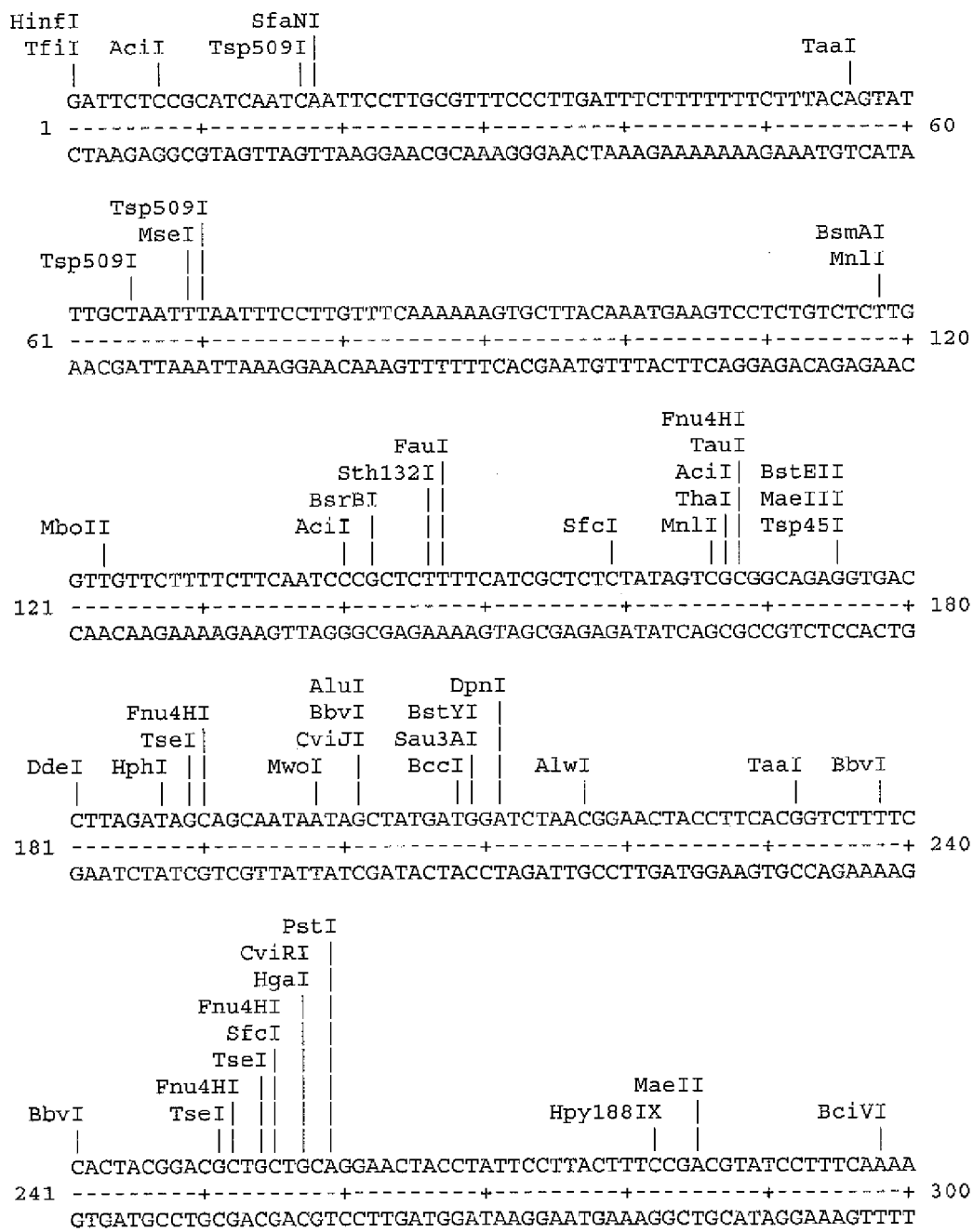
Figure 2. Restriction enzyme analysis of the *C. pneumoniae* 98 kDa outer membrane protein gene.

Figure 2B

```
              HinfI                 BsrI                   Hpy188IX
           TfiI                  Tsp509I Tsp509I        DdeI
            |                     |       |              | |
           ATCTGTGGGGAATCTATCTCTAACTGGCAATTCCCAAATTATATTTACTCAGAACTTCTC
   541    ---------+---------+---------+---------+---------+---------+  600
           TAGACACCCCTTAGATAGAGATTGACCGTTAAGGGTTTAATATAAATGAGTCTTGAAGAG Hpy188IX
     BseMII|       AciI         BcefI    XmnI                         DdeI
       ||          |             |        |                            |
           GTCAGATAACGGCGGTGTTATCAATACGAAAAACTTCTTATTATCAGGGACATCTCAGTT
   601    ---------+---------+---------+---------+---------+---------+  660
           CAGTCTATTGCCGCCACAATAGTTATGCTTTTTGAAGAATAATAGTCCCTGTAGAGTCAA Hpy178III
                   TaqI  |
            BseMII  |    |
             AluI   |    |
             CviJI  |    |
           Cac8I    |    |
      BsmFI  |      |    |       CviJI    BslI       AciI         SfcI
        |    |      |    |         |       |          |            |
           TGCGAGCTTTTCGAGAAACCAAGCCTTCACAGGGAAGCAAGGCGGTGTAGTTTACGCTAC
   661    ---------+---------+---------+---------+---------+---------+  720
           ACGCTCGAAAAGCTCTTTGGTTCGGAAGTGTCCCTTCGTTCCGCCACATCAAATGCGATG ScrFI
                             BsaJI|
                             BsaJI||
              Hpy178III  EcoRII|||                         BfaI
            CjePI TaqI  |  CviJI|||             CjePI CjePI     |
              |    |    |    ||||                |     |        |
           AGGAACTATAACTATCGAGAACAGCCCTGGGATAGTTTCCTTCTCTCAAAACCTAGCGAA
   721    ---------+---------+---------+---------+---------+---------+  780
           TCCTTGATATTGATAGCTCTTGTCGGGACCCTATCAAAGGAAGAGAGTTTTGGATCGCTT CjePI
                         RsaI  |
                      BsrGI   |
                       TatI   |
                    BsiHKAI   |
         DpnI      Bsp1286I   |            TaqI
       BstYI |    AlwI   |    |         TaaI  |
      Sau3AI |   AciI|   |    |      TspRI    |             Sau3AI
         |   |   | |    |    |        |      |               |
           AGGATCTGGCGGTGCTCTGTACAGCACTGACAACTGTTCGATTACAGATAACTTTCAAGT
   781    ---------+---------+---------+---------+---------+---------+  840
           TCCTAGACCGCCACGAGACATGTCGTGACTGTTGACAAGCTAATGTCTATTGAAAGTTCA
```

Figure 2C

```
                                    Bpu10I
                                     DdeI
                                    AluI|
                                    CviJI|
                                    FauI|
                                  Sth132I||
                                    MwoI |||
                                   SmlI | |||
                                  BsrBI| |||
                                   AciI || |||
                                  Fnu4HI|| |||
                                   TauI || |||
                                   CviJI| |||              BseMII
         Tth111II                   MwoI || |||             CviJI  |
    DpnI    |       Bce83I  BcefI|| |||    AciI    |    |   CviRI
     |      |         |       || || |||     |      |    |     |
         GATCTTTGACGGCAATAGTGCTTGGGAAGCCGCTCAAGCTCAGGGCGGGGCTATTTGTTG
   841  ---------+---------+---------+---------+---------+---------+  900
         CTAGAAACTGCCGTTATCACGAACCCTTCGGCGAGTTCGAGTCCCGCCCCGATAAACAAC TspRI
                            HinfI  |
                           MaeIII  |  |
                            TaaI   |  |
                           Tsp45I  |  |
                            PleI   |  |
                    Bsp24I  |      |  |                 CjeI
                     CjeI   |      |  |      BsrI      CjePI|
       Pfl1108I      CjePI  |      |  |  BmrI   |    Bsp24I||    MnlI
         |             |    |      |  |    |    |      |||        |
         CACTACGACAGATAAAACAGTGACTCTTACTGGGAACAAAAACCTCTCTTTCACAAATAA
   901  ---------+---------+---------+---------+---------+---------+  960
         GTGATGCTGTCTATTTTGTCACTGAGAATGACCCTTGTTTTTGGAGAGAAAGTGTTTATT AhdI
                                   HaeIV|
                                   Hin4I|
                                    SmlI ||
                                  HinfI  | ||
                                  BspGI| | ||
                               Hpy178III|| | ||
                                  PleI  ||| | ||                AvaII
                             BccI   |   ||| | ||             EcoO109I
                                CviJI   | ||| | ||             Psp5II
                              NlaIV|    | ||| | ||             Sau96I
                             Bce83I |   | ||| | ||            Sse8647I
                               EciI |   | ||| | ||    MspA1I      |
                        NdeI  AciI||    | ||| | ||     AciI       |
                          |     |||     | ||| | ||     MnlI|      |
         TACAGCATTGACATATGGCGGAGCCATCTCTGGACTCAAGGTCAGTATTTCCGCTGGAGG
   961  ---------+---------+---------+---------+---------+---------+  1020
         ATGTCGTAACTGTATACCGCCTCGGTAGAGACCTGAGTTCCAGTCATAAAGGCGACCTCC
```

Figure 2H

```
                                                          FauI
                                                          NlaIII
                                                          Sth132I|
                                                          BsaJI  ||
                                                          BstDSI ||
                                                          HgiEII ||        FauI    AciI
            ApoI                    CjeI                  NcoI   ||     Sth132I| MspAlI
        Tsp509I                    HinfI  |               StyI   ||        EciI||  CjeI|
        MboII |XmnI SfcI            TfiI  |               AciI   ||        AciI||  MwoI ||
            |    |  |                 |   |                  |   ||           ||      |||
            AATTGCGAATTTCTTCTATAGAGATTCTATGCCCACCCGCCATGGTTTCCGCCATATCAG
    2041    ---------+---------+---------+---------+---------+---------+    2100
            TTAACGCTTAAAGAAGATATCTCTAAGATACGGGTGGGCGGTACCAAAGGCGGTATAGTC
```

```
                                                              AlwI
                                                              AluI |
                                                              CviJI |
                            DpnI                      DpnI         |
                          Sau3AI  |                 Sau3AI         |
                          BfaI    |                  BsaJI         |
                   CviRI    |    |       AlwI  MnlI    |           |
                      |     |    |         |     |     |           |
                      CGGGGGTTATGCACTAGGGATCACAGCAACAACTCCTGCCGAGGATCAGCTTACTTTTGC
    2101    ---------+---------+---------+---------+---------+---------+    2160
            GCCCCCAATACGTGATCCCTAGTGTCGTTGTTGAGGACGGCTCCTAGTCGAATGAAAACG
```

```
                              BsaBI
                              DpnI   |
                  AluI      Sau3AI    |                  BsaJI
                  CviJI     AceIII   ||                  BstDSI
                  Cac8I  |  BfaI    |||                  DrdII|
                     |   |    |||   |                      ||
                  CTTCTGCCAGCTCTTTGCTAGAGATCGCAATCATATTACAGGTAAGAACCACGGAGATAC
    2161    ---------+---------+---------+---------+---------+---------+    2220
            GAAGACGGTCGAGAAACGATCTCTAGCGTTAGTATAATGTCCATTCTTGGTGCCTCTATG
```

```
                                                      EarI
                                                      SapI
                                              TaqI    |
                NlaIV                       BanII     |
             BanI |                        Bsp1286I   |
            TaaI  |           MnlI    MboII CviJI  |  |  Tsp509I
              |   |             |       |     ||   |  |     |
              TTACGGTGCCTCTTTGTATTTCCACCATACAGAAGGGCTCTTCGACATCGCCAATTTCCT
    2221    ---------+---------+---------+---------+---------+---------+    2280
            AATGCCACGGAGAAACATAAAGGTGGTATGTCTTCCCGAGAAGCTGTAGCGGTTAAAGGA
```

Figure 2K

```
         NlaIII
         TaqII         |                                 Tsp509I
         BslI|         |         Tsp509I       MboII     Hpy178III   |
         MboII|        | RleAI   |             RsaI      XmnI        | |
         |||           | |       |             |         |           | |
         CCACATGGAAATCTTCGGTCAATTCGCTTTTGAAGTACGAAGTTCTTCACGAAATTATAA
    2821 ---------+---------+---------+---------+---------+---------+ 2880
         GGTGTACCTTTAGAAGCCAGTTAAGCGAAAACTTCATGCTTCAAGAAGTGCTTTAATATT

Tsp509I
                     DdeI                                  MseI|
                CviJI    |                                 PacI|
             BfaI    |   |                                 VspI|
         AvrII|      |   |    Hpy178III          Tsp509I       ||
         BsaJI|      |   |    BfaI|       AflIII |             ||
         StyI|       |   |    XbaI||   TaqI MaeII MseI|        ||
         ||          |   |    |||       |    |    ||          ||
         TACAAACCTAGGCTCTAAGTTTTGTTTCTAGATTATCGAAAACGTGTTAATTAATTGAAC
    2881 ---------+---------+---------+---------+---------+---------+ 2940
         ATGTTTGGATCCGAGATTCAAAACAAAGATCTAATAGCTTTTGCACAATTAATTAACTTG

MaeIII
                                            PleI              Tsp45I
                                       DpnI |                 PshAI |
                                    Sau3AI  | |       EarI        | |
                   Tth111II         Hpy178III | |      Hinfl      | |
                SfaNI  |     CviRI   MboII  | | |     TaqI        | |
                |      |        |     ||||  | | |     |           | |
         CCAAGCATCTTTCTATGAAAATACCCTTGCACAAACTCCTGATCTCTTCGACTCTTGTCA
    2941 ---------+---------+---------+---------+---------+---------+ 3000
         GGTTCGTAGAAAGATACTTTTATGGGAACGTGTTTGAGGACTAGAGAAGCTGAGAACAGT CviRI
                   BsrDI  |SfaNI
                      |   |  |
         CTCCCATTCTATTGAGCATTGCAACTTACGGAGCAGATGCTTCTTTATCC
    3001 ---------+---------+---------+---------+---------+ 3050
         GAGGGTAAGATAACTCGTAACGTTGAATGCCTCGTCTACGAAGAAATAGG
```

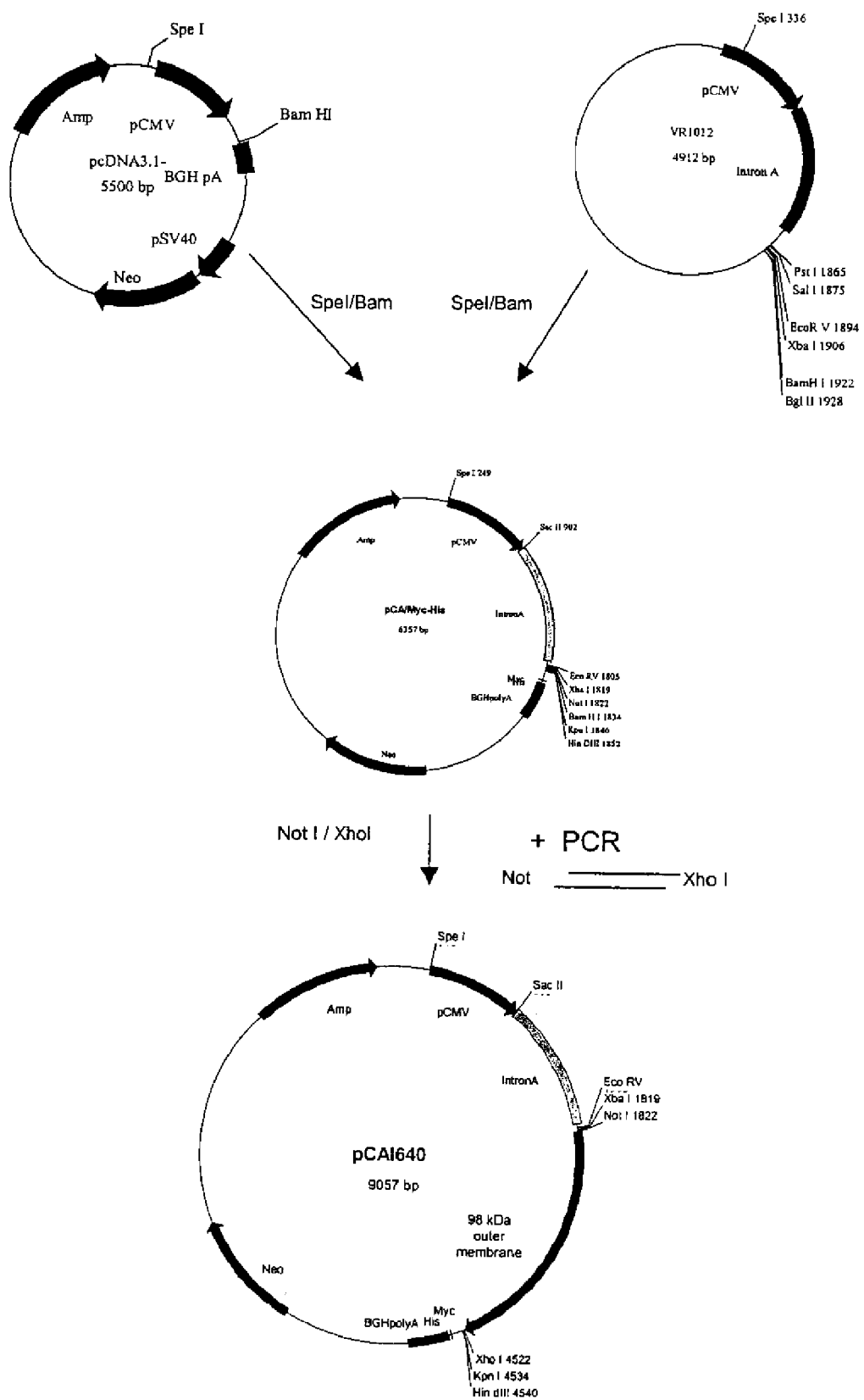
Figure 3 Construction of pCAI640

Figure 4: DNA immunization with expression plasmid pCAI640 protects against *C. pneumoniae* infection.

SEQUENCE LISTING

<160> NUMBER OF SEQ ID NOS: 6

<210> SEQ ID NO 1
<211> LENGTH: 3050
<212> TYPE: DNA
<213> ORGANISM: Chlamydia pneumoniae
<220> FEATURE:
<221> NAME/KEY: CDS
<222> LOCATION: (101)..(2908)

<400> SEQUENCE: 1

```
gattctccgc atcaatcaat tccttgcgtt tcccttgatt tcttttttc tttacagtat      60 ttgctaattt aatttccttg tttcaaaaaa gtgcttacaa atg aag tcc tct gtc     115
                                              Met Lys Ser Ser Val
                                                1               5 tct tgg ttg ttc ttt tct tca atc ccg ctc ttt tca tcg ctc tct ata     163
Ser Trp Leu Phe Phe Ser Ser Ile Pro Leu Phe Ser Ser Leu Ser Ile
             10                  15                  20 gtc gcg gca gag gtg acc tta gat agc agc aat aat agc tat gat gga     211
Val Ala Ala Glu Val Thr Leu Asp Ser Ser Asn Asn Ser Tyr Asp Gly
         25                  30                  35 tct aac gga act acc ttc acg gtc ttt tcc act acg gac gct gct gca     259
Ser Asn Gly Thr Thr Phe Thr Val Phe Ser Thr Thr Asp Ala Ala Ala
     40                  45                  50 gga act acc tat tcc tta ctt tcc gac gta tcc ttt caa aat gca ggg     307
Gly Thr Thr Tyr Ser Leu Leu Ser Asp Val Ser Phe Gln Asn Ala Gly
 55                  60                  65 gct tta gga att ccc tta gcc tca gga tgc ttc cta gaa gcg ggc ggc     355
Ala Leu Gly Ile Pro Leu Ala Ser Gly Cys Phe Leu Glu Ala Gly Gly
 70                  75                  80                  85 gat ctt act ttc caa gga aat caa cat gca ctg aag ttt gca ttt atc     403
Asp Leu Thr Phe Gln Gly Asn Gln His Ala Leu Lys Phe Ala Phe Ile
                 90                  95                 100 aat gcg ggc tct agc gct gga act gta gcc agt acc tca gca gca gat     451
```

```
                Asn Ala Gly Ser Ser Ala Gly Thr Val Ala Ser Thr Ser Ala Ala Asp
                                105                 110                 115 aag aat ctt ctc ttt aat gat ttt tct aga ctc tct att atc tct tgt       499
Lys Asn Leu Leu Phe Asn Asp Phe Ser Arg Leu Ser Ile Ile Ser Cys
        120                 125                 130 ccc tct ctt ctt ctc tct cct act gga caa tgt gct tta aaa tct gtg       547
Pro Ser Leu Leu Leu Ser Pro Thr Gly Gln Cys Ala Leu Lys Ser Val
135                 140                 145 ggg aat cta tct cta act ggc aat tcc caa att ata ttt act cag aac       595
Gly Asn Leu Ser Leu Thr Gly Asn Ser Gln Ile Ile Phe Thr Gln Asn
150                 155                 160                 165 ttc tcg tca gat aac ggc ggt gtt atc aat acg aaa aac ttc tta tta       643
Phe Ser Ser Asp Asn Gly Gly Val Ile Asn Thr Lys Asn Phe Leu Leu
            170                 175                 180 tca ggg aca tct cag ttt gcg agc ttt tcg aga aac caa gcc ttc aca       691
Ser Gly Thr Ser Gln Phe Ala Ser Phe Ser Arg Asn Gln Ala Phe Thr
                185                 190                 195 ggg aag caa ggc ggt gta gtt tac gct aca gga act ata act atc gag       739
Gly Lys Gln Gly Gly Val Val Tyr Ala Thr Gly Thr Ile Thr Ile Glu
        200                 205                 210 aac agc cct ggg ata gtt tcc ttc tct caa aac cta gcg aaa gga tct       787
Asn Ser Pro Gly Ile Val Ser Phe Ser Gln Asn Leu Ala Lys Gly Ser
215                 220                 225 ggc ggt gct ctg tac agc act gac aac tgt tcg att aca gat aac ttt       835
Gly Gly Ala Leu Tyr Ser Thr Asp Asn Cys Ser Ile Thr Asp Asn Phe
230                 235                 240                 245 caa gtg atc ttt gac ggc aat agt gct tgg gaa gcc gct caa gct cag       883
Gln Val Ile Phe Asp Gly Asn Ser Ala Trp Glu Ala Ala Gln Ala Gln
            250                 255                 260 ggc ggg gct att tgt tgc act acg aca gat aaa aca gtg act ctt act       931
Gly Gly Ala Ile Cys Cys Thr Thr Thr Asp Lys Thr Val Thr Leu Thr
                265                 270                 275 ggg aac aaa aac ctc tct ttc aca aat aat aca gca ttg aca tat ggc       979
Gly Asn Lys Asn Leu Ser Phe Thr Asn Asn Thr Ala Leu Thr Tyr Gly
        280                 285                 290 gga gcc atc tct gga ctc aag gtc agt att tcc gct gga ggt cct act      1027
Gly Ala Ile Ser Gly Leu Lys Val Ser Ile Ser Ala Gly Gly Pro Thr
295                 300                 305 cta ttt caa agt aat atc tca gga agt agc gcc ggt cag gga gga gga      1075
Leu Phe Gln Ser Asn Ile Ser Gly Ser Ser Ala Gly Gln Gly Gly Gly
310                 315                 320                 325 gga gcg atc aat ata gca tct gct ggg gaa ctc gct ctc tct gct act      1123
Gly Ala Ile Asn Ile Ala Ser Ala Gly Glu Leu Ala Leu Ser Ala Thr
            330                 335                 340 tct gga gat att acc ttc aat aac aac caa gtc acc aac gga agc aca      1171
Ser Gly Asp Ile Thr Phe Asn Asn Asn Gln Val Thr Asn Gly Ser Thr
                345                 350                 355 agt aca aga aac gca ata aat atc att gat acc gct aaa gtc aca tcg      1219
Ser Thr Arg Asn Ala Ile Asn Ile Ile Asp Thr Ala Lys Val Thr Ser
        360                 365                 370 ata cga gct gct acg ggg caa tct atc tat ttc tat gat ccc atc aca      1267
Ile Arg Ala Ala Thr Gly Gln Ser Ile Tyr Phe Tyr Asp Pro Ile Thr
375                 380                 385 aat cca gga acc gca gct tct acc gac aca ttg aac tta aac tta gca      1315
Asn Pro Gly Thr Ala Ala Ser Thr Asp Thr Leu Asn Leu Asn Leu Ala
390                 395                 400                 405 gat gcg aac agt gag atc gag tat ggg ggt gcg att gtc ttt tct gga      1363
Asp Ala Asn Ser Glu Ile Glu Tyr Gly Gly Ala Ile Val Phe Ser Gly
            410                 415                 420
```

```
                                            -continued
gaa aag ctt tcc cct aca gaa aaa gca atc gct gca aac gtc acc tct      1411
Glu Lys Leu Ser Pro Thr Glu Lys Ala Ile Ala Ala Asn Val Thr Ser
            425                 430                 435 act atc cga caa cct gca gta tta gcg cgg gga gat ctt gta ctt cgt      1459
Thr Ile Arg Gln Pro Ala Val Leu Ala Arg Gly Asp Leu Val Leu Arg
        440                 445                 450 gat gga gtc acc gta act ttc aag gat ctg act caa agt cca gga tcc      1507
Asp Gly Val Thr Val Thr Phe Lys Asp Leu Thr Gln Ser Pro Gly Ser
455                 460                 465 cgc atc tta atg gat ggg ggg act aca ctt agt gct aaa gag gca aat      1555
Arg Ile Leu Met Asp Gly Gly Thr Thr Leu Ser Ala Lys Glu Ala Asn
470                 475                 480                 485 ctt tcg ctt aat ggc tta gca gta aat ctc tcc tct tta gat gga acc      1603
Leu Ser Leu Asn Gly Leu Ala Val Asn Leu Ser Ser Leu Asp Gly Thr
                490                 495                 500 aac aag gca gct tta aaa aca gaa gct gca gat aaa aat atc agc cta      1651
Asn Lys Ala Ala Leu Lys Thr Glu Ala Ala Asp Lys Asn Ile Ser Leu
            505                 510                 515 tcg gga acg att gcg ctt att gac acg gaa ggg tca ttc tat gag aat      1699
Ser Gly Thr Ile Ala Leu Ile Asp Thr Glu Gly Ser Phe Tyr Glu Asn
        520                 525                 530 cat aac tta aaa agt gct agt acc tat cct ctt ctt gaa ctt acc acc      1747
His Asn Leu Lys Ser Ala Ser Thr Tyr Pro Leu Leu Glu Leu Thr Thr
535                 540                 545 gca gga gcc aac gga acg att act ctg gga gct ctt tct acc ctg act      1795
Ala Gly Ala Asn Gly Thr Ile Thr Leu Gly Ala Leu Ser Thr Leu Thr
550                 555                 560                 565 ctt caa gaa cct gaa acc cac tac ggg tat caa gga aac tgg cag ttg      1843
Leu Gln Glu Pro Glu Thr His Tyr Gly Tyr Gln Gly Asn Trp Gln Leu
                570                 575                 580 tct tgg gca aat gca aca tcc tca aaa ata gga agc atc aac tgg acc      1891
Ser Trp Ala Asn Ala Thr Ser Ser Lys Ile Gly Ser Ile Asn Trp Thr
            585                 590                 595 cgt aca gga tac att cct agt cct gag aga aaa agt aat ctc cct cta      1939
Arg Thr Gly Tyr Ile Pro Ser Pro Glu Arg Lys Ser Asn Leu Pro Leu
        600                 605                 610 aat agc tta tgg gga aac ttt ata gat ata cgc tcg atc aat cag ctt      1987
Asn Ser Leu Trp Gly Asn Phe Ile Asp Ile Arg Ser Ile Asn Gln Leu
615                 620                 625 ata gaa acc aag tcc agt ggg gag cct ttt gag cgt gag cta tgg ctt      2035
Ile Glu Thr Lys Ser Ser Gly Glu Pro Phe Glu Arg Glu Leu Trp Leu
630                 635                 640                 645 tca gga att gcg aat ttc ttc tat aga gat tct atg ccc acc cgc cat      2083
Ser Gly Ile Ala Asn Phe Phe Tyr Arg Asp Ser Met Pro Thr Arg His
                650                 655                 660 ggt ttc cgc cat atc agc ggg ggt tat gca cta ggg atc aca gca aca      2131
Gly Phe Arg His Ile Ser Gly Gly Tyr Ala Leu Gly Ile Thr Ala Thr
            665                 670                 675 act cct gcc gag gat cag ctt act ttt gcc ttc tgc cag ctc ttt gct      2179
Thr Pro Ala Glu Asp Gln Leu Thr Phe Ala Phe Cys Gln Leu Phe Ala
        680                 685                 690 aga gat cgc aat cat att aca ggt aag aac cac gga gat act tac ggt      2227
Arg Asp Arg Asn His Ile Thr Gly Lys Asn His Gly Asp Thr Tyr Gly
695                 700                 705 gcc tct ttg tat ttc cac cat aca gaa ggg ctc ttc gac atc gcc aat      2275
Ala Ser Leu Tyr Phe His His Thr Glu Gly Leu Phe Asp Ile Ala Asn
710                 715                 720                 725 ttc ctc tgg gga aaa gca acc cga gct ccc tgg gtg ctc tct gag atc      2323
Phe Leu Trp Gly Lys Ala Thr Arg Ala Pro Trp Val Leu Ser Glu Ile
                730                 735                 740
```

```
tcc cag atc att cct tta tcg ttc gat gct aaa ttc agt tat ctc cat      2371
Ser Gln Ile Ile Pro Leu Ser Phe Asp Ala Lys Phe Ser Tyr Leu His
        745                 750                 755 aca gac aac cac atg aag aca tat tat acc gat aac tct atc atc aag      2419
Thr Asp Asn His Met Lys Thr Tyr Tyr Thr Asp Asn Ser Ile Ile Lys
            760                 765                 770 ggt tct tgg aga aac gat gcc ttc tgt gca gat ctt gga gct agc ctg      2467
Gly Ser Trp Arg Asn Asp Ala Phe Cys Ala Asp Leu Gly Ala Ser Leu
    775                 780                 785 cct ttt gtt att tcc gtt ccg tat ctt ctg aaa gaa gtc gaa cct ttt      2515
Pro Phe Val Ile Ser Val Pro Tyr Leu Leu Lys Glu Val Glu Pro Phe
790                 795                 800                 805 gtc aaa gta cag tat atc tat gcg cat cag caa gac ttc tac gag cgt      2563
Val Lys Val Gln Tyr Ile Tyr Ala His Gln Gln Asp Phe Tyr Glu Arg
                810                 815                 820 cat gct gaa gga cgc gct ttc aat aaa agc gag ctt atc aac gta gag      2611
His Ala Glu Gly Arg Ala Phe Asn Lys Ser Glu Leu Ile Asn Val Glu
            825                 830                 835 att cct ata ggc gtc acc ttc gaa aga gac tca aaa tca gaa aag gga      2659
Ile Pro Ile Gly Val Thr Phe Glu Arg Asp Ser Lys Ser Glu Lys Gly
        840                 845                 850 act tac gat ctt act ctt atg tat ata ctc gat gct tac cga cgc aat      2707
Thr Tyr Asp Leu Thr Leu Met Tyr Ile Leu Asp Ala Tyr Arg Arg Asn
855                 860                 865 cct aaa tgt caa act tcc cta ata gct agc gat gct aac tgg atg gcc      2755
Pro Lys Cys Gln Thr Ser Leu Ile Ala Ser Asp Ala Asn Trp Met Ala
870                 875                 880                 885 tat ggt acc aac ctc gca cga caa ggt ttt tct gtt cgt gct gcg aac      2803
Tyr Gly Thr Asn Leu Ala Arg Gln Gly Phe Ser Val Arg Ala Ala Asn
                890                 895                 900 cat ttc caa gtg aac ccc cac atg gaa atc ttc ggt caa ttc gct ttt      2851
His Phe Gln Val Asn Pro His Met Glu Ile Phe Gly Gln Phe Ala Phe
            905                 910                 915 gaa gta cga agt tct tca cga aat tat aat aca aac cta ggc tct aag      2899
Glu Val Arg Ser Ser Ser Arg Asn Tyr Asn Thr Asn Leu Gly Ser Lys
        920                 925                 930 ttt tgt ttc tagattatcg aaaacgtgtt aattaattga acccaagcat              2948
Phe Cys Phe
    935 ctttctatga aaatacccct gcacaaactc ctgatctctt cgactcttgt cactcccatt   3008 ctattgagca ttgcaactta cggagcagat gcttctttat cc                      3050

<210> SEQ ID NO 2
<211> LENGTH: 2808
<212> TYPE: DNA
<213> ORGANISM: Chlamydia pneumoniae
<220> FEATURE:
<221> NAME/KEY: CDS
<222> LOCATION: (1)..(2808)

<400> SEQUENCE: 2
atgaagtcct ctgtctcttg gttgttcttt tcttcaatcc cgctctttc atcgctctct     60 atagtcgcgg cagaggtgac cttagatagc agcaataata gctatgatgg atctaacgga   120
actaccttca cggtcttttc cactacggac gctgctgcag aactaccta ttccttactt    180 tccgacgtat cctttcaaaa tgcaggggct ttaggaattc ccttagcctc aggatgcttc   240
ctagaagcgg gcggcgatct tactttccaa ggaaatcaac atgcactgaa gtttgcattt   300
atcaatgcgg gctctagcgc tggaactgta gccagtacct cagcagcaga taagaatctt   360
```

```
ctctttaatg attttctag actctctatt atctcttgtc cctctcttct tctctctcct      420
actggacaat gtgctttaaa atctgtgggg aatctatctc taactggcaa ttcccaaatt      480
atatttactc agaacttctc gtcagataac ggcggtgtta tcaatacgaa aaacttctta      540
ttatcaggga catctcagtt tgcgagcttt tcgagaaacc aagccttcac agggaagcaa      600
ggcggtgtag tttacgctac aggaactata actatcgaga acagccctgg gatagtttcc      660
ttctctcaaa acctagcgaa aggatctggc ggtgctctgt acagcactga caactgttcg      720
attacagata acttcaagt gatctttgac ggcaatagtg cttgggaagc cgctcaagct      780
cagggcgggg ctatttgttg cactacgaca gataaaacag tgactcttac tgggaacaaa      840
aacctctctt tcacaaataa tacagcattg acatatggcg gagccatctc tggactcaag      900
gtcagtattt ccgctggagg tcctactcta tttcaaagta atatctcagg aagtagcgcc      960
ggtcagggag gaggaggagc gatcaatata gcatctgctg gggaactcgc tctctctgct     1020
acttctggag atattacctt caataacaac caagtcacca acggaagcac aagtacaaga     1080
aacgcaataa atatcattga taccgctaaa gtcacatcga tacgagctgc tacggggcaa     1140
tctatctatt tctatgatcc cattcacaaa tccaggaacc gcagcttcta ccgacacatt     1200
gaacttaaac ttagcagatg cgaacagtga gatcgagtat gggggtgcga ttgtcttttc     1260
tggagaaaag ctttccccta cagaaaaagc aatcgctgca aacgtcacct ctactatccg     1320
acaacctgca gtattagcgc ggggagatct tgtacttcgt gatggagtca ccgtaacttt     1380
caaggatctg actcaaagtc caggatcccg catcttaatg gatgggaggg atacacttag     1440
tgctaaagag gcaaatcttt cgcttaatgg cttagcagta atctctcct ctttagatgg      1500 aaccaacaag gcagctttaa aaacagaagc tgcagataaa aatatcagcc tatcgggaac     1560
gattgcgctt attgacacgg aagggtcatt ctatgagaat cataacttaa aaagtgctag     1620
tacctatcct cttcttgaac ttaccaccgc aggagccaac ggaacgatta ctctgggagc     1680 tcttctctacc ctgactcttc aagaacctga aacccactac gggtacaagg aaactggcag     1740
ttgtcttggg caaatgcaac atcctcaaaa ataggaagca tcaactggac ccgtacagga     1800
tacattccta gtcctgagag aaaaagtaat ctccctctaa atagcttatg gggaaacttt     1860
atagatatac gctcgatcaa tcagcttata gaaaccaagt ccagtgggga gccttttgag     1920
cgtgagctat ggctttcagg aattgcgaat ttcttctata gagattctat gcccacccgc     1980
catggtttcc gccatatcag cgggggttat gcactaggga tcacagcaac aactcctgcc     2040
gaggatcagc ttactttgc cttctgccag ctctttgcta gagatcgcaa tcatattaca      2100
ggtaagaacc acggagatac ttacggtgcc tctttgtatt tccaccatac agaagggctc     2160
ttcgacatcg ccaatttcct ctggggaaaa gcaacccgag ctccctgggt gctctctgag     2220
atctcccaga tcattccttt atcgttcgat gctaaattca gttatctcca tacagacaac     2280
cacatgaaga catattatac cgataactct atcatcaagg gttcttggag aaacgatgcc     2340
ttctgtgcag atcttggagc tagcctgcct tttgttattt ccgttccgta acttctgaaa     2400
gaagtcgaac cttttgtcaa agtacagtat atctatgcgc atcagcaaga cttctacgag     2460
cgtcatgctg aaggacgcgc tttcaataaa agcgagctta tcaacgtaga gattcctata     2520
ggcgtcacct tcgaaagaga ctcaaaatca gaaaagggaa cttacgatct tactcttatg     2580
tatatactcg atgcttaccg acgcaatcct aaatgtcaaa cttccctaat agctagcgat     2640
gctaactgga tggcctatgg taccaacctc gcacgacaag gttttctgt tcgtgctgcg      2700
```

-continued

```
aaccatttcc aagtgaaccc ccacatggaa atcttcggtc aattcgcttt tgaagtacga    2760
agttcttcac gaaattataa tacaaaccta ggctctaagt tttgtttc                 2808
```

<210> SEQ ID NO 3
<211> LENGTH: 936
<212> TYPE: PRT
<213> ORGANISM: Chlamydia pneumoniae

<400> SEQUENCE: 3

```
Met Lys Ser Ser Val Ser Trp Leu Phe Phe Ser Ser Ile Pro Leu Phe
  1               5                  10                  15

Ser Ser Leu Ser Ile Val Ala Ala Glu Val Thr Leu Asp Ser Ser Asn
             20                  25                  30

Asn Ser Tyr Asp Gly Ser Asn Gly Thr Thr Phe Thr Val Phe Ser Thr
         35                  40                  45

Thr Asp Ala Ala Ala Gly Thr Thr Tyr Ser Leu Leu Ser Asp Val Ser
     50                  55                  60

Phe Gln Asn Ala Gly Ala Leu Gly Ile Pro Leu Ala Ser Gly Cys Phe
 65                  70                  75                  80

Leu Glu Ala Gly Gly Asp Leu Thr Phe Gln Gly Asn Gln His Ala Leu
                 85                  90                  95

Lys Phe Ala Phe Ile Asn Ala Gly Ser Ser Ala Gly Thr Val Ala Ser
            100                 105                 110

Thr Ser Ala Ala Asp Lys Asn Leu Leu Phe Asn Asp Phe Ser Arg Leu
        115                 120                 125

Ser Ile Ile Ser Cys Pro Ser Leu Leu Leu Ser Pro Thr Gly Gln Cys
    130                 135                 140

Ala Leu Lys Ser Val Gly Asn Leu Ser Leu Thr Gly Asn Ser Gln Ile
145                 150                 155                 160

Ile Phe Thr Gln Asn Phe Ser Ser Asp Asn Gly Gly Val Ile Asn Thr
                165                 170                 175

Lys Asn Phe Leu Leu Ser Gly Thr Ser Gln Phe Ala Ser Phe Ser Arg
            180                 185                 190

Asn Gln Ala Phe Thr Gly Lys Gln Gly Gly Val Val Tyr Ala Thr Gly
        195                 200                 205

Thr Ile Thr Ile Glu Asn Ser Pro Gly Ile Val Ser Phe Ser Gln Asn
    210                 215                 220

Leu Ala Lys Gly Ser Gly Gly Ala Leu Tyr Ser Thr Asp Asn Cys Ser
225                 230                 235                 240

Ile Thr Asp Asn Phe Gln Val Ile Phe Asp Gly Asn Ser Ala Trp Glu
                245                 250                 255

Ala Ala Gln Ala Gln Gly Gly Ala Ile Cys Cys Thr Thr Thr Asp Lys
            260                 265                 270

Thr Val Thr Leu Thr Gly Asn Lys Asn Leu Ser Phe Thr Asn Asn Thr
        275                 280                 285

Ala Leu Thr Tyr Gly Gly Ala Ile Ser Gly Leu Lys Val Ser Ile Ser
    290                 295                 300

Ala Gly Gly Pro Thr Leu Phe Gln Ser Asn Ile Ser Gly Ser Ser Ala
305                 310                 315                 320

Gly Gln Gly Gly Gly Gly Ala Ile Asn Ile Ala Ser Ala Gly Glu Leu
                325                 330                 335

Ala Leu Ser Ala Thr Ser Gly Asp Ile Thr Phe Asn Asn Asn Gln Val
            340                 345                 350

Thr Asn Gly Ser Thr Ser Thr Arg Asn Ala Ile Asn Ile Ile Asp Thr
```

```
            355                 360                 365
Ala Lys Val Thr Ser Ile Arg Ala Ala Thr Gly Gln Ser Ile Tyr Phe
    370                 375                 380

Tyr Asp Pro Ile Thr Asn Pro Gly Thr Ala Ala Ser Thr Asp Thr Leu
385                 390                 395                 400

Asn Leu Asn Leu Ala Asp Ala Asn Ser Glu Ile Glu Tyr Gly Gly Ala
                405                 410                 415

Ile Val Phe Ser Gly Glu Lys Leu Ser Pro Thr Glu Lys Ala Ile Ala
            420                 425                 430

Ala Asn Val Thr Ser Thr Ile Arg Gln Pro Ala Val Leu Ala Arg Gly
                435                 440                 445

Asp Leu Val Leu Arg Asp Gly Val Thr Val Thr Phe Lys Asp Leu Thr
450                 455                 460

Gln Ser Pro Gly Ser Arg Ile Leu Met Asp Gly Thr Thr Leu Ser
465                 470                 475                 480

Ala Lys Glu Ala Asn Leu Ser Leu Asn Gly Leu Ala Val Asn Leu Ser
                485                 490                 495

Ser Leu Asp Gly Thr Asn Lys Ala Ala Leu Lys Thr Glu Ala Ala Asp
            500                 505                 510

Lys Asn Ile Ser Leu Ser Gly Thr Ile Ala Leu Ile Asp Thr Glu Gly
            515                 520                 525

Ser Phe Tyr Glu Asn His Asn Leu Lys Ser Ala Ser Thr Tyr Pro Leu
            530                 535                 540

Leu Glu Leu Thr Thr Ala Gly Ala Asn Gly Thr Ile Thr Leu Gly Ala
545                 550                 555                 560

Leu Ser Thr Leu Thr Leu Gln Glu Pro Glu Thr His Tyr Gly Tyr Gln
                565                 570                 575

Gly Asn Trp Gln Leu Ser Trp Ala Asn Ala Thr Ser Ser Lys Ile Gly
            580                 585                 590

Ser Ile Asn Trp Thr Arg Thr Gly Tyr Ile Pro Ser Pro Glu Arg Lys
            595                 600                 605

Ser Asn Leu Pro Leu Asn Ser Leu Trp Gly Asn Phe Ile Asp Ile Arg
            610                 615                 620

Ser Ile Asn Gln Leu Ile Glu Thr Lys Ser Ser Gly Glu Pro Phe Glu
625                 630                 635                 640

Arg Glu Leu Trp Leu Ser Gly Ile Ala Asn Phe Phe Tyr Arg Asp Ser
                645                 650                 655

Met Pro Thr Arg His Gly Phe Arg His Ile Ser Gly Gly Tyr Ala Leu
            660                 665                 670

Gly Ile Thr Ala Thr Thr Pro Ala Glu Asp Gln Leu Thr Phe Ala Phe
            675                 680                 685

Cys Gln Leu Phe Ala Arg Asp Arg Asn His Ile Thr Gly Lys Asn His
            690                 695                 700

Gly Asp Thr Tyr Gly Ala Ser Leu Tyr Phe His His Thr Glu Gly Leu
705                 710                 715                 720

Phe Asp Ile Ala Asn Phe Leu Trp Gly Lys Ala Thr Arg Ala Pro Trp
                725                 730                 735

Val Leu Ser Glu Ile Ser Gln Ile Ile Pro Leu Ser Phe Asp Ala Lys
            740                 745                 750

Phe Ser Tyr Leu His Thr Asp Asn His Met Lys Thr Tyr Tyr Thr Asp
            755                 760                 765

Asn Ser Ile Ile Lys Gly Ser Trp Arg Asn Asp Ala Phe Cys Ala Asp
            770                 775                 780
```

-continued

```
Leu Gly Ala Ser Leu Pro Phe Val Ile Ser Val Pro Tyr Leu Leu Lys
785                 790                 795                 800

Glu Val Glu Pro Phe Val Lys Val Gln Tyr Ile Tyr Ala His Gln Gln
                805                 810                 815

Asp Phe Tyr Glu Arg His Ala Glu Gly Arg Ala Phe Asn Lys Ser Glu
            820                 825                 830

Leu Ile Asn Val Glu Ile Pro Ile Gly Val Thr Phe Glu Arg Asp Ser
        835                 840                 845

Lys Ser Glu Lys Gly Thr Tyr Asp Leu Thr Leu Met Tyr Ile Leu Asp
850                 855                 860

Ala Tyr Arg Arg Asn Pro Lys Cys Gln Thr Ser Leu Ile Ala Ser Asp
865                 870                 875                 880

Ala Asn Trp Met Ala Tyr Gly Thr Asn Leu Ala Arg Gln Gly Phe Ser
                885                 890                 895

Val Arg Ala Ala Asn His Phe Gln Val Asn Pro His Met Glu Ile Phe
            900                 905                 910

Gly Gln Phe Ala Phe Glu Val Arg Ser Ser Arg Asn Tyr Asn Thr
        915                 920                 925

Asn Leu Gly Ser Lys Phe Cys Phe
930                 935
```

<210> SEQ ID NO 4
<211> LENGTH: 925
<212> TYPE: PRT
<213> ORGANISM: Chlamydia pneumoniae

<400> SEQUENCE: 4

```
Ser Ile Pro Leu Phe Ser Ser Leu Ser Ile Val Ala Ala Glu Val Thr
1               5                   10                  15

Leu Asp Ser Ser Asn Ser Tyr Asp Gly Ser Asn Gly Thr Thr Phe
            20                  25                  30

Thr Val Phe Ser Thr Thr Asp Ala Ala Ala Gly Thr Thr Tyr Ser Leu
        35                  40                  45

Leu Ser Asp Val Ser Phe Gln Asn Ala Gly Ala Leu Gly Ile Pro Leu
    50                  55                  60

Ala Ser Gly Cys Phe Leu Glu Gly Gly Asp Leu Thr Phe Gln Gly
65                  70                  75              80

Asn Gln His Ala Leu Lys Phe Ala Phe Ile Asn Ala Gly Ser Ser Ala
                85                  90                  95

Gly Thr Val Ala Ser Thr Ser Ala Ala Asp Lys Asn Leu Leu Phe Asn
            100                 105                 110

Asp Phe Ser Arg Leu Ser Ile Ile Ser Cys Pro Ser Leu Leu Leu Ser
        115                 120                 125

Pro Thr Gly Gln Cys Ala Leu Lys Ser Val Gly Asn Leu Ser Leu Thr
    130                 135                 140

Gly Asn Ser Gln Ile Ile Phe Thr Gln Asn Phe Ser Ser Asp Asn Gly
145                 150                 155                 160

Gly Val Ile Asn Thr Lys Asn Phe Leu Ser Gly Thr Ser Gln Phe
                165                 170                 175

Ala Ser Phe Ser Arg Asn Gln Ala Phe Thr Gly Lys Gln Gly Gly Val
            180                 185                 190

Val Tyr Ala Thr Gly Thr Ile Thr Ile Glu Asn Ser Pro Gly Ile Val
        195                 200                 205

Ser Phe Ser Gln Asn Leu Ala Lys Gly Ser Gly Gly Ala Leu Tyr Ser
```

-continued

```
                 210                 215                 220
Thr Asp Asn Cys Ser Ile Thr Asp Asn Phe Gln Val Ile Phe Asp Gly
225                 230                 235                 240

Asn Ser Ala Trp Glu Ala Ala Gln Ala Gln Gly Gly Ala Ile Cys Cys
                245                 250                 255

Thr Thr Thr Asp Lys Thr Val Thr Leu Thr Gly Asn Lys Asn Leu Ser
            260                 265                 270

Phe Thr Asn Asn Thr Ala Leu Thr Tyr Gly Gly Ala Ile Ser Gly Leu
        275                 280                 285

Lys Val Ser Ile Ser Ala Gly Gly Pro Thr Leu Phe Gln Ser Asn Ile
    290                 295                 300

Ser Gly Ser Ser Ala Gly Gln Gly Gly Gly Ala Ile Asn Ile Ala
305                 310                 315                 320

Ser Ala Gly Glu Leu Ala Leu Ser Ala Thr Ser Gly Asp Ile Thr Phe
                325                 330                 335

Asn Asn Asn Gln Val Thr Asn Gly Ser Thr Ser Thr Arg Asn Ala Ile
            340                 345                 350

Asn Ile Ile Asp Thr Ala Lys Val Thr Ser Ile Arg Ala Ala Thr Gly
        355                 360                 365

Gln Ser Ile Tyr Phe Tyr Asp Pro Ile Thr Asn Pro Gly Thr Ala Ala
    370                 375                 380

Ser Thr Asp Thr Leu Asn Leu Asn Leu Ala Asp Ala Asn Ser Glu Ile
385                 390                 395                 400

Glu Tyr Gly Gly Ala Ile Val Phe Ser Gly Glu Lys Leu Ser Pro Thr
                405                 410                 415

Glu Lys Ala Ile Ala Ala Asn Val Thr Ser Thr Ile Arg Gln Pro Ala
            420                 425                 430

Val Leu Ala Arg Gly Asp Leu Val Leu Arg Asp Gly Val Thr Val Thr
        435                 440                 445

Phe Lys Asp Leu Thr Gln Ser Pro Gly Ser Arg Ile Leu Met Asp Gly
    450                 455                 460

Gly Thr Thr Leu Ser Ala Lys Glu Ala Asn Leu Ser Leu Asn Gly Leu
465                 470                 475                 480

Ala Val Asn Leu Ser Ser Leu Asp Gly Thr Asn Lys Ala Ala Leu Lys
                485                 490                 495

Thr Glu Ala Ala Asp Lys Asn Ile Ser Leu Ser Gly Thr Ile Ala Leu
            500                 505                 510

Ile Asp Thr Glu Gly Ser Phe Tyr Glu Asn His Asn Leu Lys Ser Ala
        515                 520                 525

Ser Thr Tyr Pro Leu Leu Glu Leu Thr Thr Ala Gly Ala Asn Gly Thr
    530                 535                 540

Ile Thr Leu Gly Ala Leu Ser Thr Leu Thr Leu Gln Glu Pro Glu Thr
545                 550                 555                 560

His Tyr Gly Tyr Gln Gly Asn Trp Gln Leu Ser Trp Ala Asn Ala Thr
                565                 570                 575

Ser Ser Lys Ile Gly Ser Ile Asn Trp Thr Arg Thr Gly Tyr Ile Pro
            580                 585                 590

Ser Pro Glu Arg Lys Ser Asn Leu Pro Leu Asn Ser Leu Trp Gly Asn
        595                 600                 605

Phe Ile Asp Ile Arg Ser Ile Asn Gln Leu Ile Glu Thr Lys Ser Ser
    610                 615                 620

Gly Glu Pro Phe Glu Arg Glu Leu Trp Leu Ser Gly Ile Ala Asn Phe
625                 630                 635                 640
```

```
Phe Tyr Arg Asp Ser Met Pro Thr Arg His Gly Phe Arg His Ile Ser
                645                 650                 655

Gly Gly Tyr Ala Leu Gly Ile Thr Ala Thr Thr Pro Ala Glu Asp Gln
            660                 665                 670

Leu Thr Phe Ala Phe Cys Gln Leu Phe Ala Arg Asp Arg Asn His Ile
        675                 680                 685

Thr Gly Lys Asn His Gly Asp Thr Tyr Gly Ala Ser Leu Tyr Phe His
    690                 695                 700

His Thr Glu Gly Leu Phe Asp Ile Ala Asn Phe Leu Trp Gly Lys Ala
705                 710                 715                 720

Thr Arg Ala Pro Trp Val Leu Ser Glu Ile Ser Gln Ile Ile Pro Leu
                725                 730                 735

Ser Phe Asp Ala Lys Phe Ser Tyr Leu His Thr Asp Asn His Met Lys
            740                 745                 750

Thr Tyr Tyr Thr Asp Asn Ser Ile Ile Lys Gly Ser Trp Arg Asn Asp
        755                 760                 765

Ala Phe Cys Ala Asp Leu Gly Ala Ser Leu Pro Phe Val Ile Ser Val
    770                 775                 780

Pro Tyr Leu Leu Lys Glu Val Glu Pro Phe Val Lys Val Gln Tyr Ile
785                 790                 795                 800

Tyr Ala His Gln Gln Asp Phe Tyr Glu Arg His Ala Glu Gly Arg Ala
                805                 810                 815

Phe Asn Lys Ser Glu Leu Ile Asn Val Glu Ile Pro Ile Gly Val Thr
            820                 825                 830

Phe Glu Arg Asp Ser Lys Ser Glu Lys Gly Thr Tyr Asp Leu Thr Leu
        835                 840                 845

Met Tyr Ile Leu Asp Ala Tyr Arg Arg Asn Pro Lys Cys Gln Thr Ser
    850                 855                 860

Leu Ile Ala Ser Asp Ala Asn Trp Met Ala Tyr Gly Thr Asn Leu Ala
865                 870                 875                 880

Arg Gln Gly Phe Ser Val Arg Ala Ala Asn His Phe Gln Val Asn Pro
                885                 890                 895

His Met Glu Ile Phe Gly Gln Phe Ala Phe Glu Val Arg Ser Ser Ser
            900                 905                 910

Arg Asn Tyr Asn Thr Asn Leu Gly Ser Lys Phe Cys Phe
        915                 920                 925

<210> SEQ ID NO 5
<211> LENGTH: 43
<212> TYPE: DNA
<213> ORGANISM: Artificial Sequence
<220> FEATURE:
<223> OTHER INFORMATION: primer (5')

<400> SEQUENCE: 5
ataagaatgc ggccgccacc atggcagagg tgaccttaga tag                       43

<210> SEQ ID NO 6
<211> LENGTH: 31
<212> TYPE: DNA
<213> ORGANISM: Artificial Sequence
<220> FEATURE:
<223> OTHER INFORMATION: primer (3')

<400> SEQUENCE: 6
cggctcgagt gaaacaaaac ttagagccta g                                    31
```

CHLAMYDIA POLYPEPTIDES AND CORRESPONDING DNA FRAGMENTS AND USES THEREOF

REFERENCE TO RELATED APPLICATIONS

This application is a divisional application of U.S. application Ser. No. 10/324,129, filed Dec. 20, 2002, now U.S. Pat. No. 7,326,545, which is a continuation of U.S. application Ser. No. 09/452,380, filed Dec. 1, 1999, now abandoned, and which claims the benefit of U.S. Provisional Application No. 60/110,439, filed Dec. 1, 1998 and U.S. Provisional Application No. 60/132,272, filed May 3, 1999, the contents of which are hereby incorporated by reference.

FIELD OF INVENTION

The present invention relates to the *Chlamydia* 98 KDa outer membrane protein antigen and corresponding DNA molecules, which can be used to prevent and treat *Chlamydia* infection in mammals, such as humans.

BACKGROUND OF THE INVENTION

Chlamydiae are prokaryotes. They exhibit morphologic and structural similarities to gram-negative bacteria including a trilaminar outer membrane, which contains lipopolysaccharide and several membrane proteins that are structurally and functionally analogous to proteins found in *E coli*. They are obligate intra-cellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

*C. pneumoniae* is a common human pathogen, originally described as the TWAR strain of *Chlamydia psittaci* but subsequently recognised to be a new species. *C. pneumoniae* is antigenically, genetically and morphologically distinct from other *chlamydia* species (*C. trachomatis, C. pecorum* and *C. psittaci*). It shows 10% or less DNA sequence homology with either of *C. trachomatis* or *C. psittaci*.

*C. pneumoniae* is a common cause of community acquired pneumonia, only less frequent than *Streptococcus pneumoniae* and *Mycoplasma pneumoniae* (Grayston et al. (1995) Journal of Infectious Diseases 168:1231; Campos et al. (1995) Investigation of Ophthalmology and Visual Science 36:1477). It can also cause upper respiratory tract symptoms and disease, including bronchitis and sinusitis (Grayston et al. (1995) Journal of Infectious Diseases 168:1231; Grayston et al (1990) Journal of Infectious Diseases 161:618; Marrie (1993) Clinical Infectious Diseases. 18:501; Wang et al (1986) Chlamydial infections Cambridge University Press, Cambridge. p. 329. The great majority of the adult population (over 60%) has antibodies to *C. pneumoniae* (Wang et al (1986) Chlamydial infections. Cambridge University Press, Cambridge. p. 329), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from fomites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against chlamydial infections.

In most instances, *C. pneumoniae* infection is often mild and without complications, and up to 90% of infections are subacute or unrecognized. Among children in industrialized countries, infections have been thought to be rare up to the age of 5 y, although a recent study (E Normann et al, *Chlamydia pneumoniae* in children with acute respiratory tract infections, Acta Paediatrica, 1998, Vol 87, Iss 1, pp 23-27) has reported that many children in this age group show PCR evidence of infection despite being seronegative, and estimates a prevalence of 17-19% in 2-4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (Saikku et al. (1988) Lancet; ii:983; Thom et al. (1992) JAMA 268:68; Linnanmaki et al. (1993), Circulation 87:1030; Saikku et al. (1992) Annals Internal Medicine 116:273; Melnick et al (1993) American Journal of Medicine 95:499). Moreover, the organisms has been detected in atheromas and fatty streaks of the coronary, carotid, peripheral arteries and aorta (Shor et al. (1992) South African. Medical Journal 82:158; Kuo et al. (1993) Journal of Infectious Diseases 167:841; Kuo et al. (1993) Arteriosclerosis and Thrombosis 13:1500; Campbell et al (1995) Journal of Infectious Diseases 172:585; Chiu et al. Circulation, 1997 (In Press)). Viable *C. pneumoniae* has been recovered from the coronary and carotid artery (Ramirez et al (1996) Annals of Internal Medicine 125:979; Jackson et al. Abst. K121, p 272, 36$^{th}$ ICAAC, 15-18 Sep. 1996, New Orleans). Furthermore, it has been shown that *C. pneumoniae* can induce changes of atherosclerosis in a rabbit model (Fong et al (1997) Journal of Clinical Microbiology 35:48). Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (Hahn D L, et al. Evidence for *Chlamydia pneumoniae* infection in steroid-dependent asthma. Ann Allergy Asthma Immunol. 1998 January; 80 (1): 45-49; Hahn D L, et al. Association of *Chlamydia pneumoniae* IgA antibodies with recently symptomatic asthma. Epidemiol Infect. 1996 December; 117 (3): 513-517; Bjornsson E, et al. Serology of *chlamydia* in relation to asthma and bronchial hyperresponsiveness. Scand J Infect Dis. 1996; 28 (1): 63-69; Hahn D L. Treatment of *Chlamydia pneumoniae* infection in adult asthma: a before-after trial. J Fam Pract. 1995 October; 41 (4): 345-351; Allegra L, et al. Acute exacerbations of asthma in adults: role of *Chlamydia pneumoniae* infection. Eur Respir J. 1994 December; 7 (12): 2165-2168; Hahn D L, et al. Association of *Chlamydia pneumoniae* (strain TWAR) infection with wheezing, asthmatic bronchitis, and adult-onset asthma. JAMA. 1991 Jul. 10; 266 (2): 225-230).

In light of these results a protective vaccine against *C. pneumoniae* infection would be of considerable importance. There is not yet an effective vaccine for any human chlamydial infection. It is conceivable that an effective vaccine can be developed using physically or chemically inactivated Chlamydiae. However, such a vaccine does not have a high margin of safety. In general, safer vaccines are made by genetically manipulating the organism by attenuation or by recombinant means. Accordingly, a major obstacle in creating an effective and safe vaccine against human chlamydial infection has been the paucity of genetic information regarding *Chlamydia*, specifically *C. pneumoniae*.

Studies with *C. trachomatis* and *C. psittaci* indicate that safe and effective vaccine against *Chlamydia* is an attainable goal. For example, mice which have recovered from a lung infection with *C. trachomatis* are protected from infertility induced by a subsequent vaginal challenge (Pal et al. (1996) Infection and Immunity. 64:5341). Similarly, sheep immunized with inactivated *C. psittaci* were protected from subsequent chlamydial-induced abortions and stillbirths (Jones et al. (1995) Vaccine 13:715). Protection from chlamydial infections has been associated with Th1 immune responses, particularly the induction of INFg-producing CD4+ T-cells (Igietsemes et al. (1993) Immunology 5:317). The adoptive transfer of CD4+ cell lines or clones to nude or SCID mice conferred protection from challenge or cleared chronic disease (Igietseme et al (1993) Regional Immunology 5:317; Magee et al (1993) Regional Immunology 5: 305), and in vivo depletion of CD4+ T cells exacerbated disease post-challenge (Landers et al (1991) Infection & Immunity 59:3774; Magee et al (1995) Infection & Immunity 63:516). However, the presence of sufficiently high titres of neutralising antibody at mucosal surfaces can also exert a protective effect (Cotter et al. (1995) Infection and Immunity 63:4704).

Antigenic variation within the species *C. pneumoniae* is not well documented due to insufficient genetic information, though variation is expected to exist based on *C. trachomatis*. Serovars of *C. trachomatis* are defined on the basis of antigenic variation in the major outer membrane protein (MOMP), but published *C. pneumoniae* MOMP gene sequences show no variation between several diverse isolates of the organism (Campbell et al (1990) Infection and Immunity 58:93; McCafferty et al (1995) Infection and Immunity 63:2387-9; Gaydos et al (1992) Infection and Immunity. 60 (12):5319-5323). The gene encoding a 76 kDa antigen has been cloned from a single strain of *C. pneumoniae* and the sequence published (Perez Melgosa et al., Infect. Immun. 1994. 62:880). An operon encoding the 9 kDa and 60 kDa cysteine-rich outer membrane protein genes has been described (Watson et al., Nucleic Acids Res (1990) 18:5299; Watson et al., Microbiology (1995) 141:2489). Many antigens recognized by immune sera to *C. pneumoniae* are conserved across all chlamydiae, but 98 kDa, 76 kDa and several other proteins may be *C. pneumoniae*-specific (Perez Melgosa et al., Infect. Immun. 1994. 62:880; Melgosa et al., FEMS Microbiol Lett (1993) 112:199; Campbell et al., J Clin Microbiol (1990) 28:1261; Iijima et al., J Clin Microbiol (1994) 32:583). An assessment of the number and relative frequency of any *C. pneumoniae* serotypes, and the defining antigens, is not yet possible. The entire genome sequence of *C. pneumoniae* strain CWL-029 is now known and as further sequences become available a better understanding of antigenic variation may be gained.

Many antigens recognised by immune sera to *C. pneumoniae* are conserved across all chlamydiae, but 98 kDa, 76 kDa and 54 kDa proteins appear to be *C. pneumoniae*-specific (Campos et al. (1995) Investigation of Ophthalmology and Visual Science 36:1477; Marrie (1993) Clinical Infectious Diseases. 18:501; Wiedmann-Al-Ahmad M, et al. Reactions of polyclonal and neutralizing anti-p54 monoclonal antibodies with an isolated, species-specific 54-kilodalton protein of *Chlamydia pneumoniae*. Clin Diagn Lab Immunol. 1997 November; 4 (6): 700-704). Immunoblotting of isolates with sera from patients does show variation of blotting patterns between isolates, indicating that serotypes *C. pneumoniae* may exist (Grayston et al. (1995) Journal of Infectious Diseases 168:1231; Ramirez et al (1996) Annals of Internal Medicine 125:979). However, the results are potentially confounded by the infection status of the patients, since immunoblot profiles of a patient's sera change with time post-infection. An assessment of the number and relative frequency of any serotypes, and the defining antigens, is not yet possible.

Accordingly, a need exists for identifying and isolating polynucleotide sequences of *C. pneumoniae* for use in preventing and treating *Chlamydia* infection.

SUMMARY OF THE INVENTION

The present invention provides purified and isolated polynucleotide molecules that encode the *Chlamydia* 98 KDa outer membrane protein which can be used in methods to prevent, treat, and diagnose *Chlamydia* infection. In one form of the invention, the polynucleotide molecules are DNA that encode polypeptides CPN100640 (SEQ ID Nos: 1 and 2).

Another form of the invention provides polypeptides corresponding to the isolated DNA molecules. The amino acid sequences of the corresponding encoded polypeptides are shown as SEQ ID No: 3 and 4, where SEQ ID No. 3 is the full length sequence and SEQ ID No. 4 is the post-translationally processed sequence.

Those skilled in the art will readily understand that the invention, having provided the polynucleotide sequences encoding the *Chlamydia* 98 KDa outer membrane protein, also provides polynucleotides encoding fragments derived from such polypeptides. Moreover, the invention is understood to provide mutants and derivatives of such polypeptides and fragments derived therefrom, which result from the addition, deletion, or substitution of non-essential amino acids as described herein. Those skilled in the art would also readily understand that the invention, having provided the polynucleotide sequences encoding *Chlamydia* polypeptides, further provides monospecific antibodies that specifically bind to such polypeptides.

The present invention has wide application and includes expression cassettes, vectors, and cells transformed or transfected with the polynucleotides of the invention. Accordingly, the present invention further provides (i) a method for producing a polypeptide of the invention in a recombinant host system and related expression cassettes, vectors, and transformed or transfected cells; (ii) a vaccine, or a live vaccine vector such as a pox virus, *Salmonella typhimurium*, or *Vibrio cholerae* vector, containing a polynucleotide of the invention, such vaccines and vaccine vectors being useful for, e.g., preventing and treating *Chlamydia* infection, in combination with a diluent or carrier, and related pharmaceutical compositions and associated therapeutic and/or prophylactic methods; (iii) a therapeutic and/or prophylactic use of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of *Chlamydia* in a biological sample, which can involve the use of a DNA or RNA molecule, a monospecific antibody, or a polypeptide of the invention; and (v) a method for purifying a polypeptide of the invention by antibody-based affinity chromatography.

BRIEF DESCRIPTION OF THE DRAWINGS

The present invention will be further understood from the following description with reference to the drawings, in which:

FIG. 1 shows the nucleotide sequence of the CPN100640 (SEQ ID No: 1—entire sequence and SEQ ID No: 2—coding sequence) and the deduced amino acid sequence of the CPN100640 protein from *Chlamydia pneumoniae* (SEQ ID No: 3—full length and 4—processed). The sequence is encoded on the negative strand.

FIG. 2 shows the restriction enzyme analysis of the *C. pneumoniae* 98 kDa outer membrane protein gene.

FIG. 3 shows the construction and elements of plasmid pCAI640.

FIG. 4 illustrates protection against *C. pneumoniae* infection by pCAI640 following DNA immunization.

DETAILED DESCRIPTION OF INVENTION

An open reading frames (ORF) encoding the chlamydial 98 KDa outer membrane protein has been identified from the *C. pneumoniae* genome. The gene encoding this protein has been inserted into an expression plasmid and shown to confer immune protection against chlamydial infection. Accordingly, this outer membrane protein and related polypeptides can be used to prevent and treat *Chlamydia* infection.

According to a first aspect of the invention, isolated polynucleotides are provided which encode the precursor and mature forms of *Chlamydia* polypeptides, whose amino acid sequences are SEQ ID Nos: 3 and 4 respectively.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the polypeptides of the invention as shown in SEQ ID Nos: 1 and 2 is (a) a coding sequence, (b) a ribonucleotide sequence derived from transcription of (a), or (c) a coding sequence which uses the redundancy or degeneracy of the genetic code to encode the same polypeptides. By "polypeptide" or "protein" is meant any chain of amino acids, regardless of length or post-translational modification (e.g., glycosylation or phosphorylation). Both terms are used interchangeably in the present application.

Consistent with the first aspect of the invention, amino acid sequences are provided which are homologous to either SEQ ID No: 3 or 4. As used herein, "homologous amino acid sequence" is any polypeptide which is encoded, in whole or in part, by a nucleic acid sequence which hybridizes at 25-35° C. below critical melting temperature (Tm), to any portion of the nucleic acid sequences of SEQ ID Nos: 1 and 2. A homologous amino acid sequence is one that differs from an amino acid sequence shown in SEQ ID No: 3 or 4 by one or more conservative amino acid substitutions. Such a sequence also encompass serotypic variants (defined below) as well as sequences containing deletions or insertions which retain inherent characteristics of the polypeptide such as immunogenicity. Preferably, such a sequence is at least 75%, more preferably 80%, and most preferably 90% identical to SEQ ID No: 3 or 4.

Homologous amino acid sequences include sequences that are identical or substantially identical to SEQ ID No: 3 or 4. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 60%, and most preferably 85% identical to either coding sequence SEQ ID Nos: 1 or 2.

Consistent with the first aspect of the invention, polypeptides having a sequence homologous to SEQ ID No: 3 or 4 include naturally-occurring allelic variants, as well as mutants or any other non-naturally occurring variants that retain the inherent characteristics of the polypeptide of SEQ ID No: 3 or 4.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. Biological function is distinct from antigenic property. A polypeptide can have more than one biological function.

Allelic variants are very common in nature. For example, a bacterial species such as *C. pneumoniae*, is usually represented by a variety of strains that differ from each other by minor allelic variations. Indeed, a polypeptide that fulfills the same biological function in different strains can have an amino acid sequence (and polynucleotide sequence) that is not identical in each of the strains. Despite this variation, an immune response directed generally against many allelic variants has been demonstrated. In studies of the Chlamydial MOMP antigen, cross-strain antibody binding plus neutralization of infectivity occurs despite amino acid sequence variation of MOMP from strain to strain, indicating that the MOMP, when used as an immunogen, is tolerant of amino acid variations.

Polynucleotides encoding homologous polypeptides or allelic variants are retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers are designed according to the nucleotide sequence information provided in SEQ ID Nos:1 and 2. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 μL, 20 to 200 μM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for dematuration of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: $Tm=81.5+0.41\times(\%\ G+C)+16.6\ \log(\text{cation ion concentration})-0.63\times(\%\ \text{formamide})-600/\text{base number}$. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4-16 hours at 42° C., in 6×SSC containing 50% formamide, or (ii) within 4-16 hours at 65° C. in an aqueous 6×SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6×SSC, preferably in 2×SSC or 1×SSC, more preferably in 0.5×SSC, 0.3×SSC or 0.1×SSC (in the absence of formamide). 1×SSC contains 0.15 M NaCl and 0.015 M sodium citrate.

Useful homologs and fragments thereof that do not occur naturally are designed using known methods for identifying regions of an antigen that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using the BLAST homology searching algorithm of Altschul et al., Nucleic Acids Res; 25:3389-3402 (1997). Alternatively, sequences are modified such that they become more reactive to T- and/or B-cells, based on computer-assisted analysis of probable T- or B-cell epitopes Yet another alternative is to mutate a particular amino acid residue or sequence within the polypeptide in vitro, then screen the mutant polypeptides for their ability to prevent or treat *Chlamydia* infection according to the method outlined below.

A person skilled in the art will readily understand that by following the screening process of this invention, it will be determined without undue experimentation whether a particular homolog of SEQ ID No. 3 or 4 may be useful in the prevention or treatment of *Chlamydia* infection. The screening procedure comprises the steps:
(i) immunizing an animal, preferably mouse, with the test homolog or fragment;
(ii) inoculating the immunized animal with *Chlamydia*; and
(iii) selecting those homologs or fragments which confer protection against *Chlamydia*.

By "conferring protection" is meant that there is a reduction is severity of any of the effects of *Chlamydia* infection, in comparison with a control animal which was not immunized with the test homolog or fragment.

Consistent with the first aspect of the invention, polypeptide derivatives are provided that are partial sequences of SEQ ID No. 3 or 4, partial sequences of polypeptide sequences homologous to SEQ ID No. 3 or 4, polypeptides derived from full-length polypeptides by internal deletion, and fusion proteins.

It is an accepted practice in the field of immunology to use fragments and variants of protein immunogens as vaccines, as all that is required to induce an immune response to a protein is a small (e.g., 8 to 10 amino acid) immunogenic region of the protein. Various short synthetic peptides corresponding to surface-exposed antigens of pathogens other than *Chlamydia* have been shown to be effective vaccine antigens against their respective pathogens, e.g. an 11 residue peptide of murine mammary tumor virus (Casey & Davidson, Nucl. Acid Res. (1977) 4:1539), a 16-residue peptide of Semliki Forest virus (Snijders et al., 1991. J. Gen. Virol. 72:557-565), and two overlapping peptides of 15 residues each from canine parvovirus (Langeveld et al., Vaccine 12 (15):1473-1480, 1994).

Accordingly, it will be readily apparent to one skilled in the art, having read the present description, that partial sequences of SEQ ID No: 3 or 4 or their homologous amino acid sequences are inherent to the full-length sequences and are taught by the present invention. Such polypeptide fragments preferably are at least 12 amino acids in length. Advantageously, they are at least 20 amino acids, preferably at least 50 amino acids, more preferably at least 75 amino acids, and most preferably at least 100 amino acids in length.

Polynucleotides of 30 to 600 nucleotides encoding partial sequences of sequences homologous to SEQ ID No: 3 or 4 are retrieved by PCR amplification using the parameters outlined above and using primers matching the sequences upstream and downstream of the 5' and 3' ends of the fragment to be amplified. The template polynucleotide for such amplification is either the full length polynucleotide homologous to one of SEQ ID Nos: 1 and 2, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20-30 bases are to be obtained, the formula for calculating the Tm is as follows: Tm=4×(G+C)+2 (A+T). For example, an 18 nucleotide fragment of 50% G+C would have an approximate Tm of 54° C. Short peptides that are fragments of SEQ ID No: 3 or 4 or their homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Useful polypeptide derivatives, e.g., polypeptide fragments, are designed using computer-assisted analysis of amino acid sequences. This would identify probable surface-exposed, antigenic regions (Hughes et al., 1992. Infect. Immun. 60 (9):3497). Analysis of 6 amino acid sequences contained in SEQ ID No: 3 or 4, based on the product of flexibility and hydrophobicity propensities using the program SEQSEE (Wishart D S, et al. "SEQSEE: a comprehensive program suite for protein sequence analysis." *Comput Appl Biosci.* 1994 April; 10 (2):121-32), can reveal potential B- and T-cell epitopes which may be used as a basis for selecting useful immunogenic fragments and variants. This analysis uses a reasonable combination of external surface features that is likely to be recognized by antibodies. Probable T-cell epitopes for HLA-A0201 MHC subclass may be revealed by an algorithms that emulate an approach developed at the NIH (Parker K C, et al. "Peptide binding to MHC class I molecules: implications for antigenic peptide prediction." *Immunol Res* 1995; 14 (1):34-57).

Epitopes which induce a protective T cell-dependent immune response are present throughout the length of the polypeptide. However, some epitopes may be masked by secondary and tertiary structures of the polypeptide. To reveal such masked epitopes large internal deletions are created which remove much of the original protein structure and exposes the masked epitopes. Such internal deletions sometimes effects the additional advantage of removing immunodominant regions of high variability among strains. Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to prevent or treat *Chlamydia* infection as described above.

As used herein, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

An advantageous example of a fusion polypeptide is one where the polypeptide or homolog or fragment of the invention is fused to a polypeptide having adjuvant activity, such as subunit B of either cholera toxin or *E. coli* heat-labile toxin. Another advantageous fusion is one where the polypeptide, homolog or fragment is fused to a strong T-cell epitope or B-cell epitope. Such an epitope may be one known in the art (e.g. the Hepatitis B virus core antigen, D. R. Millich et al., "Antibody production to the nucleocapsid and envelope of the Hepatitis B virus primed by a single synthetic T cell site", Nature. 1987. 329:547-549), or one which has been identified in another polypeptide of the invention based on computer-assisted analysis of probable T- or B-cell epitopes. Consistent with this aspect of the invention is a fusion polypeptide comprising T- or B-cell epitopes from one of SEQ ID No: 3 or 4 or its homolog or fragment, wherein the epitopes are derived from multiple variants of said polypeptide or homolog or fragment, each variant differing from another in the location and sequence of its epitope within the polypeptide. Such a fusion is effective in the prevention and treatment of *Chlamydia* infection since it optimizes the T- and B-cell response to the overall polypeptide, homolog or fragment.

To effect fusion, the polypeptide of the invention is fused to the N-, or preferably, to the C-terminal end of the polypeptide having adjuvant activity or T- or B-cell epitope. Alternatively, a polypeptide fragment of the invention is inserted internally within the amino acid sequence of the polypeptide having adjuvant activity. The T- or B-cell epitope may also be inserted internally within the amino acid sequence of the polypeptide of the invention.

Consistent with the first aspect, the polynucleotides of the invention also encode hybrid precursor polypeptides containing heterologous signal peptides, which mature into polypeptides of the invention. By "heterologous signal peptide" is meant a signal peptide that is not found in naturally-occurring precursors of polypeptides of the invention.

A polynucleotide molecule according to the invention, including RNA, DNA, or modifications or combinations thereof, have various applications. A DNA molecule is used, for example, (i) in a process for producing the encoded polypeptide in a recombinant host system, (ii) in the construction of vaccine vectors such as poxviruses, which are further used in methods and compositions for preventing and/or treating *Chlamydia* infection, (iii) as a vaccine agent (as well as an RNA molecule), in a naked form or formulated with a delivery vehicle and, (iv) in the construction of attenuated *Chlamydia* strains that can over-express a polynucleotide of the invention or express it in a non-toxic, mutated form.

Accordingly, a second aspect of the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system is selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli*. Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form.

One skilled in the art would readily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4 (7):843)); the promoter of the gene of bacteriophage T7 encoding RNA polymerase, that is functional in a number of

*E. coli* strains expressing T7 polymerase (described in U.S. Pat. No. 4,952,496); OspA lipidation signal peptide; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

A polynucleotide of the invention can also be useful as a vaccine. There are two major routes, either using a viral or bacterial host as gene delivery vehicle (live vaccine vector) or administering the gene in a free form, e.g., inserted into a plasmid. Therapeutic or prophylactic efficacy of a polynucleotide of the invention is evaluated as described below.

Accordingly, a third aspect of the invention provides (i) a vaccine vector such as a poxvirus, containing a DNA molecule of the invention, placed under the control of elements required for expression; (ii) a composition of matter comprising a vaccine vector of the invention, together with a diluent or carrier; specifically (iii) a pharmaceutical composition containing a therapeutically or prophylactically effective amount of a vaccine vector of the invention; (iv) a method for inducing an immune response against *Chlamydia* in a mammal (e.g., a human; alternatively, the method can be used in veterinary applications for treating or preventing *Chlamydia* infection of animals, e.g., cats or birds), which involves administering to the mammal an immunogenically effective amount of a vaccine vector of the invention to elicit a protective or therapeutic immune response to *Chlamydia*; and particularly, (v) a method for preventing and/or treating a *Chlamydia* (e.g., *C. trachomatis, C. psittaci, C. pneumonia, C. pecorum*) infection, which involves administering a prophylactic or therapeutic amount of a vaccine vector of the invention to an infected individual. Additionally, the third aspect of the invention encompasses the use of a vaccine vector of the invention in the preparation of a medicament for preventing and/or treating *Chlamydia* infection.

As used herein, a vaccine vector expresses one or several polypeptides or derivatives of the invention, The vaccine vector may express additionally a cytokine, such as interleukin-2 (IL-2) or interleukin-12 (IL-12), that enhances the immune response (adjuvant effect). It is understood that each of the components to be expressed is placed under the control of elements required for expression in a mammalian cell.

Consistent with the third aspect of the invention is a composition comprising several vaccine vectors, each of them capable of expressing a polypeptide or derivative of the invention. A composition may also comprise a vaccine vector capable of expressing an additional *Chlamydia* antigen, or a subunit, fragment, homolog, mutant, or derivative thereof; optionally together with or a cytokine such as IL-2 or IL-12.

Vaccination methods for treating or preventing infection in a mammal comprises use of a vaccine vector of the invention to be administered by any conventional route, particularly to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. Treatment may be effected in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., *Shigella, Salmonella, Vibrio cholerae, Lactobacillus*, Bacille bilié de Calmette-Guérin (BCG), and *Streptococcus*.

An example of an adenovirus vector, as well as a method for constructing an adenovirus vector capable of expressing a DNA molecule of the invention, are described in U.S. Pat. No. 4,920,209. Poxvirus vectors include vaccinia and canary pox virus, described in U.S. Pat. No. 4,722,848 and U.S. Pat. No. 5,364,773, respectively. (Also see, e.g., Tartaglia et al., Virology (1992) 188:217) for a description of a vaccinia virus vector and Taylor et al, Vaccine (1995) 13:539 for a reference of a canary pox.) Poxvirus vectors capable of expressing a polynucleotide of the invention are obtained by homologous recombination as described in Kieny et al., Nature (1984) 312:163 so that the polynucleotide of the invention is inserted in the viral genome under appropriate conditions for expression in mammalian cells. Generally, the dose of vaccine viral vector, for therapeutic or prophylactic use, can be of from about $1 \times 10^4$ to about $1 \times 10^{11}$, advantageously from about $1 \times 10^7$ to about $1 \times 10^{11}$ preferably of from about $1 \times 10^7$ to about $1 \times 10^9$ plaque-forming units per kilogram. Preferably, viral vectors are administered parenterally; for example, in 3 doses, 4 weeks apart. It is preferable to avoid adding a chemical adjuvant to a composition containing a viral vector of the invention and thereby minimizing the immune response to the viral vector itself.

Non-toxicogenic *vibrio cholerae* mutant strains that are useful as a live oral vaccine are known. Mekalanos et al., Nature (1983) 306:551 and U.S. Pat. No. 4,882,278 describe strains which have a substantial amount of the coding sequence of each of the two ctxA alleles deleted so that no functional cholerae toxin is produced. WO 92/11354 describes a strain in which the irgA locus is inactivated by mutation; this mutation can be combined in a single strain with ctxA mutations. WO 94/01533 describes a deletion mutant lacking functional ctxA and attRSI DNA sequences. These mutant strains are genetically engineered to express heterologous antigens, as described in WO 94/19482. An effective vaccine dose of a *Vibrio cholexae* strain capable of expressing a polypeptide or polypeptide derivative encoded by a DNA molecule of the invention contains about $1 \times 10^5$ to about $1 \times 10^9$, preferably about $1 \times 10^6$ to about $1 \times 10^8$, viable bacteria in a volume appropriate for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al. (Bio/Technology (1988) 6:693) and WO 92/11361. Preferred routes of administration include all mucosal routes; most preferably, these vectors are administered intranasally or orally.

Other bacterial strains used as vaccine vectors in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868; and for Bacille Calmette Guerin in Flynn J. L., Cell. Mol. Biol. (1994) 40 (suppl. I):31, WO 88/06626, WO 90/00594, WO 91/13157, WO 92/01796, and WO 92/21376.

In bacterial vectors, the polynucleotide of the invention is inserted into the bacterial genome or remains in a free state as part of a plasmid.

The composition comprising a vaccine bacterial vector of the present invention may further contain an adjuvant. A number of adjuvants are known to those skilled in the art. Preferred adjuvants are selected as provided below.

Accordingly, a fourth aspect of the invention provides (i) a composition of matter comprising a polynucleotide of the invention, together with a diluent or carrier; (ii) a pharmaceutical composition comprising a therapeutically or prophylactically effective amount of a polynucleotide of the invention; (iii) a method for inducing an immune response against *Chlamydia* in a mammal by administration of an immunogenically effective amount of a polynucleotide of the invention to elicit a protective immune response to *Chlamydia*; and particularly, (iv) a method for preventing and/or treating a *Chlamydia* (e.g., *C. trachomatis*, *C. psittaci*, *C. pneumoniae*, or *C. pecorum*) infection, by administering a prophylactic or therapeutic amount of a polynucleotide of the invention to an infected individual. Additionally, the fourth aspect of the invention encompasses the use of a polynucleotide of the invention in the preparation of a medicament for preventing and/or treating *Chlamydia* infection. A preferred use includes the use of a DNA molecule placed under conditions for expression in a mammalian cell, especially in a plasmid that is unable to replicate in mammalian cells and to substantially integrate in a mammalian genome.

Use of the polynucleotides of the invention include their administration to a mammal as a vaccine, for therapeutic or prophylactic purposes. Such polynucleotides are used in the form of DNA as part of a plasmid that is unable to replicate in a mammalian cell and unable to integrate into the mammalian genome. Typically, such a DNA molecule is placed under the control of a promoter suitable for expression in a mammalian cell. The promoter functions either ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, Molec. Cell Biol. (1985) 5:281). An example of a tissue-specific promoter is the desmin promoter which drives expression in muscle cells (Li et al., Gene (1989) 78:243, Li & Paulin, J. Biol. Chem. (1991) 266:6562 and Li & Paulin, J. Biol. Chem. (1993) 268:10403). Use of promoters is well-known to those skilled in the art. Useful vectors are described in numerous publications, specifically WO 94/21797 and Hartikka et al., Human Gene Therapy (1996) 7:1205.

Polynucleotides of the invention which are used as a vaccine encode either a precursor or a mature form of the corresponding polypeptide. In the precursor form, the signal peptide is either homologous or heterologous. In the latter case, a eucaryotic leader sequence such as the leader sequence of the tissue-type plasminogen factor (tPA) is preferred.

As used herein, a composition of the invention contains one or several polynucleotides with optionally at least one additional polynucleotide encoding another *Chlamydia* antigen such as urease subunit A, B, or both, or a fragment, derivative, mutant, or analog thereof. The composition may also contain an additional polynucleotide encoding a cytokine, such as interleukin-2 (IL-2) or interleukin-12 (IL-12) so that the immune response is enhanced. These additional polynucleotides are placed under appropriate control for expression. Advantageously, DNA molecules of the invention and/or additional DNA molecules to be included in the same composition, are present in the same plasmid.

Standard techniques of molecular biology for preparing and purifying polynucleotides are used in the preparation of polynucleotide therapeutics of the invention. For use as a vaccine, a polynucleotide of the invention is formulated according to various methods outlined below.

One method utilizes the polynucleotide in a naked form, free of any delivery vehicles. Such a polynucleotide is simply diluted in a physiologically acceptable solution such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

An alternative method utilizes the polynucleotide in association with agents that assist in cellular uptake. Examples of such agents are (i) chemicals that modify cellular permeability, such as bupivacaine (see, e.g., WO 94/16737), (ii) liposomes for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides. Cationic lipids are also known in the art and are commonly used for gene delivery. Such lipids include Lipofectin™ also known as DOTMA (N-[1-(2,3-dioleyloxy)propyl]-N,N,N-trimethylammonium chloride), DOTAP (1,2-bis(oleyloxy)-3-(trimethylammonio) propane), DDAB (dimethyldioctadecylammonium bromide), DOGS (dioctadecylamidologlycyl spermine) and cholesterol derivatives such as DC-Chol (3 beta-(N—(N',N'-dimethyl aminomethane)-carbamoyl)cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles are used for gene delivery, as described in WO 91/00359, WO 93/17706, and Tang et al. Nature (1992) 356:152. The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration is any conventional route used in the vaccine field. As general guidance, a polynucleotide of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or sub-cutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that are used for diagnostic purposes. Accordingly, a fifth aspect of the invention provides a nucleotide probe or primer having a sequence found in or derived by degeneracy of the genetic code from a sequence shown in SEQ ID No:1 or 2.

The term "probe" as used in the present application refers to DNA (preferably single stranded) or RNA molecules (or modifications or combinations thereof) that hybridize under the stringent conditions, as defined above, to nucleic acid molecules having SEQ ID No:1 or 2 or to sequences homologous to SEQ ID No:1 or 2, or to their complementary or anti-sense sequences. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of SEQ ID No:1 or 2 or that are complementary to such sequences. Probes may contain modified bases such as inosine, methyl-5-deoxycytidine, deoxyuridine, dimethylamino-5-deoxyuridine, or diamino-2,6-purine. Sugar or phosphate residues may also be modified or substituted. For example, a deoxyribose residue may be replaced by a polyamide (Nielsen et al., Science (1991) 254: 1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used in diagnostic tests, as capture or detection probes. Such capture probes are conventionally immobilized on a solid support, directly or indirectly, by covalent means or by passive adsorption. A detection probe is labelled by a detection marker selected from: radioactive isotopes, enzymes such as peroxidase, alkaline phosphatase, and enzymes able to hydrolyze a chromogenic, fluorogenic, or luminescent substrate, compounds that are chromogenic, fluorogenic, or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is a probe of usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art.

As described herein, the invention also encompasses (i) a reagent comprising a probe of the invention for detecting and/or identifying the presence of *Chlamydia* in a biological material; (ii) a method for detecting and/or identifying the presence of *Chlamydia* in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of *Chlamydia* in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

It is apparent that disclosure of polynucleotide sequences of SEQ ID No:1 or 2, their homolog, and partial sequences of either enable their corresponding amino acid sequences. Accordingly, a sixth aspect of the invention features a substantially purified polypeptide or polypeptide derivative having an amino acid sequence encoded by a polynucleotide of the invention.

A "substantially purified polypeptide" as used herein is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art would readily understand that the polypeptides of the invention may be purified from a natural source, i.e., a *Chlamydia* strain, or produced by recombinant means.

Consistent with the sixth aspect of the invention are polypeptides, homologs or fragments which are modified or treated to enhance their immunogenicity in the target animal, in whom the polypeptide, homolog or fragments are intended to confer protection against *Chlamydia*. Such modifications or treatments include: amino acid substitutions with an amino acid derivative such as 3-methyhistidine, 4-hydroxyproline, 5-hydroxylysine etc., modifications or deletions which are carried out after preparation of the polypeptide, homolog or fragment, such as the modification of free amino, carboxyl or hydroxyl side groups of the amino acids.

Identification of homologous polypeptides or polypeptide derivatives encoded by polynucleotides of the invention which have specific antigenicity is achieved by screening for cross-reactivity with an antiserum raised against the polypeptide of reference having an amino acid sequence of any one of SEQ ID No:3 or 4. The procedure is as follows: a monospecific hyperimmune antiserum is raised against a purified reference polypeptide, a fusion polypeptide (for example, an expression product of MBP, GST, or His-tag systems, the description and instructions for use of which are contained in Invitrogen product manuals for pcDNA3.1/Myc-His(+) A, B, and C and for the Xpress™ System Protein Purification), or a synthetic peptide predicted to be antigenic. Where an antiserum is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmli (Nature (1970) 227:680). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 µl of a preparation at about 10 µg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 µl PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 µl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below. A seventh aspect of the invention provides (i) a composition of matter comprising a polypeptide of the invention together with a diluent or carrier; specifically (ii) a pharmaceutical composition containing a therapeutically or prophylactically effective amount of a polypeptide of the invention; (iii) a method for inducing an immune response against *Chlamydia* in a mammal, by administering to the mammal an immunogenically effective amount of a polypeptide of the invention to elicit a protective immune response to *Chlamydia*; and particularly, (iv) a method for preventing and/or treating a *Chlamydia* (e.g., *C. trachomatis. C. psittaci, C. pneumoniae*. or *C. pecorum*) infection, by administering a prophylactic or therapeutic amount of a polypeptide of the invention to an infected individual. Additionally, the seventh aspect of the invention encompasses the use of a polypeptide of the invention in the preparation of a medicament for preventing and/or treating *Chlamydia* infection.

As used herein, the immunogenic compositions of the invention are administered by conventional routes known the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of administration route depends upon a number of parameters, such as the adjuvant associated with the polypeptide. If a mucosal adjuvant is used, the intranasal or oral route is preferred. If a lipid formulation or an aluminum compound is used, the parenteral route is preferred with the sub-cutaneous or intramuscular route being most preferred. The choice also depends upon the nature of the vaccine agent. For example, a polypeptide of the invention fused to CTB or LTB is best administered to a mucosal surface.

As used herein, the composition of the invention contains one or several polypeptides or derivatives of the invention. The composition optionally contains at least one additional *Chlamydia* antigen, or a subunit, fragment, homolog, mutant, or derivative thereof.

For use in a composition of the invention, a polypeptide or derivative thereof is formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach, RCP New Ed, IRL press (1990).

Adjuvants other than liposomes and the like are also used and are known in the art. Adjuvants may protect the antigen from rapid dispersal by sequestering it in a local deposit, or they may contain substances that stimulate the host to secrete factors that are chemotactic for macrophages and other components of the immune system. An appropriate selection can conventionally be made by those skilled in the art, for example, from those described below (under the eleventh aspect of the invention).

Treatment is achieved in a single dose or repeated as necessary at intervals, as can be determined readily by one skilled in the art. For example, a priming dose is followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention is administered by a mucosal route in an amount from about 10 µg to about 500 mg, preferably from about 1 mg to about 200 mg. For the parenteral route of administration, the dose usually does not exceed about 1 mg, preferably about 100 µg.

When used as vaccine agents, polynucleotides and polypeptides of the invention may be used sequentially as part of a multistep immunization process. For example, a mammal is initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention is also used for priming, with boosting being carried out mucosally using a soluble polypeptide or derivative of the invention in combination with a mucosal adjuvant (e.g., LT).

A polypeptide derivative of the invention is also used in accordance with the seventh aspect as a diagnostic reagent for detecting the presence of anti-*Chlamydia* antibodies, e.g., in a blood sample. Such polypeptides are about 5 to about 80, preferably about 10 to about 50 amino acids in length. They are either labeled or unlabeled, depending upon the diagnostic method. Diagnostic methods involving such a reagent are described below.

Upon expression of a DNA molecule of the invention, a polypeptide or polypeptide derivative is produced and purified using known laboratory techniques. As described above, the polypeptide or polypeptide derivative may be produced as a fusion protein containing a fused tail that facilitates purification. The fusion product is used to immunize a small mammal, e.g., a mouse or a rabbit, in order to raise antibodies against the polypeptide or polypeptide derivative (monospecific antibodies). Accordingly, an eighth aspect of the invention provides a monospecific antibody that binds to a polypeptide or polypeptide derivative of the invention.

By "monospecific antibody" is meant an antibody that is capable of reacting with a unique naturally-occurring *Chlamydia* polypeptide. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the polypeptides, homologs or fragments of the present invention are generated by immunization of a mammal with a composition comprising said polypeptide, homolog or fragment. Such antibodies may be polyclonal or monoclonal. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657-680. For monoclonal antibodies, see Kohler & Milstein (1975) Nature 256:495-497.

The antibodies of the invention, which are raised to a polypeptide or polypeptide derivative of the invention, are produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies are used in diagnostic methods to detect the presence of a *Chlamydia* antigen in a sample, such as a biological sample. The antibodies are also used in affinity chromatography for purifying a polypeptide or polypeptide derivative of the invention. As is discussed further below, such antibodies may be used in prophylactic and therapeutic passive immunization methods.

Accordingly, a ninth aspect of the invention provides (i) a reagent for detecting the presence of *Chlamydia* in a biological sample that contains an antibody, polypeptide, or polypeptide derivative of the invention; and (ii) a diagnostic method for detecting the presence of *Chlamydia* in a biological sample, by contacting the biological sample with an antibody, a polypeptide, or a polypeptide derivative of the invention, such that an immune complex is formed, and by detecting such complex to indicate the presence of *Chlamydia* in the sample or the organism from which the sample is derived.

Those skilled in the art will readily understand that the immune complex is formed between a component of the sample and the antibody, polypeptide, or polypeptide derivative, whichever is used, and that any unbound material is removed prior to detecting the complex. It is understood that a polypeptide reagent is useful for detecting the presence of anti-*Chlamydia* antibodies in a sample, e.g., a blood sample, while an antibody of the invention is used for screening a sample, such as a gastric extract or biopsy, for the presence of *Chlamydia* polypeptides.

For diagnostic applications, the reagent (i.e., the antibody, polypeptide, or polypeptide derivative of the invention) is either in a free state or immobilized on a solid support, such as a tube, a bead, or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means may also employ a ligand-receptor system, for example, where a molecule such as a vitamin is grafted onto the polypeptide reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent are labeled with a detection means which allows for the detection of the reagent when it is bound to its target. The detection means may be a fluorescent agent such as fluorescein isocyanate or fluorescein isothiocyanate, or an enzyme such as horse radish peroxidase or luciferase or alkaline phosphatase, or a radioactive element such as $^{125}$I or $^{51}$Cr.

Accordingly, a tenth aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody is either polyclonal or monospecific, and preferably is of the IgG type. Purified IgGs is prepared from an antiserum using standard methods (see, e.g., Coligan et al., Current Protocols in Immunology (1994) John Wiley & Sons, Inc., New York, N.Y.). Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as an *C. pneumoniae* extract preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An eleventh aspect of the invention provides (i) a composition of matter comprising a monospecific antibody of the invention, together with a diluent or carrier; (ii) a pharmaceutical composition comprising a therapeutically or prophylactically effective amount of a monospecific antibody of the invention, and (iii) a method for treating or preventing a *Chlamydia* (e.g., *C. trachomatis*, *C. psittaci*, *C. pneumoniae* or *C. pecorum*) infection, by administering a therapeutic or prophylactic amount of a monospecific antibody of the invention to an infected individual. Additionally, the eleventh aspect of the invention encompasses the use of a monospecific antibody of the invention in the preparation of a medicament for treating or preventing *Chlamydia* infection.

The monospecific antibody is either polyclonal or monoclonal, preferably of the IgA isotype (predominantly). In passive immunization, the antibody is administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, is carried out. A monospecific antibody of the invention is administered as a single active component or as a mixture with at least one monospecific antibody specific for a different *Chlamydia* polypeptide. The amount of antibody and the particular regimen used are readily determined by one skilled in the art. For example, daily administration of about 100 to 1,000 mg of antibodies over one week, or three doses per day of about 100 to 1,000 mg of antibodies over two or three days, are effective regimens for most purposes.

Therapeutic or prophylactic efficacy are evaluated using standard methods in the art, e.g., by measuring induction of a mucosal immune response or induction of protective and/or therapeutic immunity, using, e.g., the *C. pneumoniae* mouse model. Those skilled in the art will readily recognize that the *C. pneumoniae* strain of the model may be replaced with another *Chlamydia* strain. For example, the efficacy of DNA molecules and polypeptides from *C. pneumoniae* is preferably evaluated in a mouse model using *C. pneumoniae* strain. Protection is determined by comparing the degree of *Chlamydia* infection to that of a control group. Protection is shown when infection is reduced by comparison to the control group. Such an evaluation is made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), is used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/06627 (Arg-192-Gly LT mutant), and WO 95/34323 (Arg-9-Lys and Glu-129-Gly PT mutant). Additional LT mutants that are used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli*, *Salmonella minnesota*, *Salmonella typhimurium*, or *Shigella flexneri*; saponins, or polylactide glycolide (PLGA) microspheres, is also be used in mucosal administration.

Adjuvants useful for both mucosal and parenteral administrations include polyphosphazene (WO 95/02415), DC-chol (3 b-(N—(N',N'-dimethyl aminomethane)-carbamoyl)cholesterol; U.S. Pat. No. 5,283,185 and WO 96/14831) and QS-21 (WO 88/09336).

Any pharmaceutical composition of the invention containing a polynucleotide, a polypeptide, a polypeptide derivative, or an antibody of the invention, is manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which *Chlamydia* infection are treated by oral administration of a *Chlamydia* polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together, are used. The invention also includes compositions for carrying out these methods, i.e., compositions containing a *Chlamydia* antigen (or antigens) of the invention, an adjuvant, and one or more of the above-listed compounds, in a pharmaceutically acceptable carrier or diluent.

It has recently been shown that the 60 kDa cysteine rich membrane protein contains a sequence cross-reactive with the murine alpha-myosin heavy chain epitope M7A-alpha, an epitope conserved in humans (Bachmaier et al., Science (1999) 283:1335). This cross-reactivity is proposed to contribute to the development of cardiovascular disease, so it may be beneficial to remove this epitope, and any other epitopes cross-reactive with human antigens, from the protein if it is to be used as a vaccine. Accordingly, a further embodiment of the present invention includes the modification of the coding sequence, for example, by deletion or substitution of the nucleotides encoding the epitope from polynucleotides encoding the protein, as to improve the efficacy and safety of the protein as a vaccine. A similar approach may be appropriate for any protective antigen found to have unwanted homologies or cross-reactivities with human antigens.

Amounts of the above-listed compounds used in the methods and compositions of the invention are readily determined by one skilled in the art. Treatment/immunization schedules are also known and readily designed by one skilled in the art. For example, the non-vaccine components can be administered on days 1-14, and the vaccine antigen+adjuvant can be administered on days 7, 14, 21, and 28.

EXAMPLES

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This example illustrates the preparation of the eukaryotic expression vector pCA/Myc-His.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His.

Example 2

This example illustrates the preparation of a plasmid expression vector containing the 98 kDa outer membrane protein gene.

The 98 kDa outer membrane protein gene was amplified from *Chlamydia pneumoniae* genomic DNA by polymerase chain reaction (PCR) using a 5' primer (5' ATAAGAAT GCGGCCGCCACCATGGCAGAGGTGACCTTAGATAG 3') (SEQ ID No:5) and a 3' primer (5' CGG CTCGAGTGAAACAAAACTTAGAGCCTAG 3') (SEQ ID No:6). The 5' primer contains a Not I restriction site, a ribosome binding site, an initiation codon and a sequence at the 5' end of the 98 kDa outer membrane protein coding sequence. The 3' primer includes the sequence encoding the C-terminal sequence of the 98 kDa outer membrane protein gene and a Xho I restriction site. The stop codon was excluded and an additional nucleotide was inserted to obtain an in-frame fusion with the Histidine tag.

After amplification, the PCR fragment was purified using QIAquick™ PCR purification kit (Qiagen) and then digested with Not I and Xho I. The Not I/Xho I restricted PCR fragment containing the 98 kDa outer membrane protein gene was ligated into the Not I and Xho I restricted plasmid pCA/Myc-His to produce plasmid pCAI640 (FIG. 3). Transcription of the 98 KDa outer membrane protein gene in pCAIG40 was under control of the human cytomegalovirus (CMV) promoter.

The plasmid pCAI640, was transferred by electroporation into *E. coli* XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and ethidium bromide staining and comparison to molecular weight standards. The 5' and 3' ends of the gene were verified by sequencing using a LiCor model 4000 L DNA sequencer and IRD-800 labelled primers.

Example 3

This example illustrates the immunization of mice to achieve protection against an intranasal challenge of *C. pneumoniae*.

It has been previously demonstrated (Yang, Z. P., Chi, E. Y., Kuo, C. C. and Grayston, J. T. 1993. A mouse model of *C. pneumoniae* strain TWAR pneumonitis. 61 (5):2037-2040) that mice are susceptible to intranasal infection with different isolates of *C. pneumoniae*. Strain AR-39 (Chi, E. Y., Kuo, C. C. and Grayston, J. T., 1987. Unique ultrastructure in the elementary body of *Chlamydia* sp. strain TWAR. J. Bacteriol. 169 (8):3757-63) was used in Balb/c mice as a challenge infection model to examine the capacity of *chlamydia* gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (8 to 10 per group) were immunized intramuscularly (i.m.) plus intranasally (i.n.) with plasmid DNA containing the coding sequence of *C. pneumoniae* 98 kDa outer membrane protein gene as described in Example 1 and 2. Saline or the plasmid vector lacking an inserted chlamydial gene was given to groups of control animals.

For i.m. immunization alternate left and right quadriceps were injected with 100 μg of DNA in 50 μl of PBS on three occasions at 0, 3 and 6 weeks. For i.n. immunization, anaesthetized mice aspirated 50 μl of PBS containing 50 μg DNA on three occasions at 0, 3 and 6 weeks. At week 8, immunized mice were inoculated i.n. with $5\times10^5$ IFU of *C. pneumoniae*, strain AR39 in 100 μl of SPG buffer to test their ability to limit the growth of a sublethal *C. pneumoniae* challenge.

Lungs were taken from mice at days 5 and 9 post-challenge and immediately homogenised in SPG buffer (7.5% sucrose, 5 mM glutamate, 12.5 mM phosphate pH7.5). The homogenate was stored frozen at −70° C. until assay. Dilutions of the homogenate were assayed for the presence of infectious chlamydia by inoculation onto monolayers of susceptible cells. The inoculum was centrifuged onto the cells at 3000 rpm for 1 hour, then the cells were incubated for three days at 35° C. in the presence of 1 μg/ml cycloheximide. After incubation the monolayers were fixed with formalin and methanol then immunoperoxidase stained for the presence of chlamydial inclusions using convalescent sera from rabbits infected with *C. pneumoniae* and metal-enhanced DAB as a peroxidase substrate.

Table 1 and FIG. 4 show that mice immunized i.n. and i.m. with pCAI640 had chlamydial lung titers less than 255,000 in 4 of 4 cases at day 5 and less than 423,200 in 4 of 4 cases at day 9 whereas the range of values for control mice sham immunized with saline was 227,000-934,200 IFU/lung (mean 685, 240) at day 5 and 96,000-494,000 IFU/lung (mean 238,080) at day 9. DNA immunisation per se was not responsible for the observed protective effect since another plasmid DNA construct, pCAI634, failed to protect, with lung titers in immunised mice similar to those obtained for saline-immunized control mice. The construct pCAI634 is identical to pCAI640 except that the nucleotide sequence encoding the 98 kDa outer membrane protein gene is replaced with a *C. pneumoniae* nucleotide sequence encoding a different putative 98 kDa outer membrane protein.

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS
IMMUNIZING CONSTRUCT

| MOUSE | Saline Day 5 | Saline Day 9 | pCAI634 Day 5 | pCAI634 Day 9 | pCAI640 Day 5 | pCAI640 Day 9 |
|---|---|---|---|---|---|---|
| 1 | 934200 | 494000 | 1228400 | 151900 | 143100 | 373700 |
| 2 | 638800 | 180500 | 203300 | 70900 | 204800 | 291000 |
| 3 | 226800 | 245400 | 92900 | 567000 | 196600 | 404500 |
| 4 | 908800 | 174500 | 348600 | 628800 | 254600 | 423200 |
| 5 | 717600 | 96000 | | | | |
| MEAN | 685240 | 238080 | 468300 | 354650 | 199775 | 373100 |
| SD | 285189.07 | 152555.91 | 517439.29 | 283943.87 | 45655.11 | 58414.44 |

The invention claimed is:

1. An isolated nucleic acid molecule comprising a nucleotide sequence which encodes the polypeptide SEQ ID NO:3 or 4.

2. The isolated nucleic acid molecule of claim 1 comprising the nucleotide sequence SEQ ID NO: 1 or 2.

3. An isolated nucleic acid molecule which encodes a fusion protein, said fusion protein comprising the polypeptide encoded by the nucleic acid molecule of claim 1 as a first polypeptide and a second polypeptide which is heterologous to the first polypeptide.

4. The nucleic acid molecule of claim 3 wherein the second polypeptide is a heterologous signal peptide.

5. The nucleic acid molecule of claim 3 wherein the second polypeptide has adjuvant activity.

6. The nucleic acid molecule of claim 1, operably linked to one or more expression control sequences.

7. The nucleic acid molecule of claim 2, operably linked to one or more expression control sequences.

8. A vaccine vector comprising a nucleotide sequence which encodes the polypeptide of SEQ ID NO:3 or 4, wherein the nucleotide sequence is operably linked to a promoter functional in a mammalian cell, wherein the vaccine vector is unable to replicate in mammalian cells and unable to integrate in a mammalian genome.

9. The vaccine vector of claim 8 comprising the nucleotide sequence SEQ ID NO:1 or 2 operably linked to a promoter functional in a mammalian cell.

10. A vaccine vector comprising the nucleic acid molecule of claim 3 operably linked to a promoter functional in a mammalian cell, wherein the vaccine vector is unable to replicate in mammalian cells and unable to integrate in a mammalian genome.

11. The vaccine vector of claim 8 wherein the promoter is a viral promoter.

12. The vaccine vector of claim 9 wherein the promoter is a viral promoter.

13. The vaccine vector of claim 10 wherein the promoter is a viral promoter.

14. The vaccine vector of claim 8 wherein the promoter is cytomegalovirus (CMV) promoter.

15. The vaccine vector of claim 9 wherein the promoter is cytomegalovirus (CMV) promoter.

16. The vaccine vector of claim 10 wherein the promoter is cytomegalovirus (CMV) promoter.

17. The vaccine vector of claim 8 further comprising another nucleotide sequence encoding an additional polypeptide which enhances the immune response to the polypeptide having SEQ ID NO:3 or 4, wherein the additional polypeptide is a *Chlamydia* polypeptide.

18. A pharmaceutical composition comprising the nucleic acid of claim 1 and a pharmaceutically acceptable carrier.

19. A pharmaceutical composition comprising the vaccine vector of claim 8 and a pharmaceutically acceptable carrier.

20. The composition of claim 19 further comprising an adjuvant.

21. A pharmaceutical composition comprising the vaccine vector of claim 9 and a pharmaceutically acceptable carrier.

22. The composition of claim 21 further comprising an adjuvant.

23. The vaccine vector according to claim 8 in unit dosage form.

24. The vaccine vector according to claim 9 in unit dosage form.

25. The vaccine vector according to claim 11 in unit dosage form.

26. The vaccine vector according to claim 12 in unit dosage form.

* * * * *